US006934579B2

(12) United States Patent
Mantzaridis et al.

(10) Patent No.: US 6,934,579 B2
(45) Date of Patent: Aug. 23, 2005

(54) ANAESTHESIA CONTROL SYSTEM

(75) Inventors: Haralambos Mantzaridis, Glasgow (GB); Gavin N. C. Kenny, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 0 days.

(21) Appl. No.: 09/973,568

(22) Filed: Oct. 9, 2001

(65) Prior Publication Data

US 2002/0117176 A1 Aug. 29, 2002

Related U.S. Application Data

(63) Continuation of application No. 09/267,932, filed on Mar. 11, 1999, now abandoned, which is a continuation of application No. PCT/GB97/02435, filed on Sep. 10, 1997.

(30) Foreign Application Priority Data

Sep. 11, 1996  (GB) .............................................. 9618998

(51) Int. Cl.[7] .................................................. A61B 5/04
(52) U.S. Cl. ..................................................... 600/544
(58) Field of Search .............................. 600/544, 54.5; 128/203.13, 204.23

(56) References Cited

U.S. PATENT DOCUMENTS

| | | | |
|---|---|---|---|
| 2,690,178 A | 9/1954 | Bickford | 128/213 |
| 4,280,494 A | 7/1981 | Cosgrove, Jr. et al. | 128/213 R |
| 4,557,270 A | 12/1985 | John | 128/731 |
| 5,699,808 A | 12/1997 | John | 128/731 |
| 5,775,330 A | 7/1998 | Kangas et al. | 128/731 |
| 6,016,444 A | 1/2000 | John | 600/544 |
| 6,067,467 A | 5/2000 | John | 600/544 |

FOREIGN PATENT DOCUMENTS

| | | |
|---|---|---|
| WO | WO 91/19453 | 12/1991 |
| WO | WO 93/07804 | 4/1993 |

OTHER PUBLICATIONS

De Beere et al. May, 1996; British Journal of Anaesthesia; 76: 685–693.*
Webb et al., *Closed–Loop Control of Depth of Anaesthesia*, Measurement + Control, vol. 29, No. 7, Sep. 1996, pp. 211–215.

(Continued)

*Primary Examiner*—Eric F. Winakur
*Assistant Examiner*—Jonathan Foreman
(74) *Attorney, Agent, or Firm*—Nixon & Vanderhye, PC

(57) ABSTRACT

An anaesthesia control system and a method of calculating an index representative of the depth of anaesthesia is disclosed. The method comprises subjecting a patient to a repetitive audio stimulus and monitoring and auditory evoked potentials (AEP) produced by the patient and then recording these auditory evoked potentials using EEG recording means and providing a signal corresponding to the coarseness of the monitored AEP signal and using this signal as an index indicative of anaesthetic depth. The raw AEP signal is divided into a series of sweeps and each sweep is synchronized with the repetitive audio stimulus and sweeps are recorded in sequence to produce a time averaged sweep from which the anaesthetic index is calculated. The anaesthetic index is constantly updated by repeatedly conducting a successive series of sweeps. The system and index signal can be used as part of an anaesthesia control system for regulating the supply of anaesthetic to the patient to maintain the anaesthetic index at a predetermined level.

30 Claims, 6 Drawing Sheets

OTHER PUBLICATIONS

International Search Report, PCT/GB97/02435, Feb. 3, 1998.

Sebel et al., "The Cebrel Function Analysis Monitor (CFAM): A New Microprocessor–based Device for the On–line Analysis of the EEG and Evoked Potentials," British Journal of Anaesthesia (1983), vol. 55, No. 12, pp. 1265–1270.

Kochs, E., "Electrophysiological monitoring and mild hypothermia," Journal of Neurosurgical Anaesthesiology (1995), vol. 7, No. 3, pp. 222–228.

Schwender et al., "Spectral edge frequency of the electroencephalogram to monitor "depth" of anaesthesia with isoflurane or propofol," British Journal of Anaesthesia (1996), vol. 77, No. 2, pp. 179–184.

Leslie et al., "Prediction of movement during propofol/nitrous oxide anesthesia," Anesthesiology (1996), vol. 84, No. 1; pp. 52–63.

Gaitini et al., "Awareness detection during caesarean section under general anaesthesia using EEG spectrum analysis," Canadian Journal of Anaesthesia (1995), vol. 42, No. 5, pp. 37–381.

Traast et al., "Electroencephalographic characteristics of emergence from propofol/sufentanil total intravenous anesthesia," Anesthesia and Analgesia (1995), vol. 81, No. 2, pp. 366–371.

Schwilden et al., "Closed–loop feedback control of propofol anaesthesia by quantitative EEG analysis in humans," British Journal of Anaesthesiology, (1989), vol. 62, No. 3, pp. 290–296.

Russ et al., "Spectral analysis of the EEG during hypothermic cardiopulmonary bypass," Acta Anaesthesiologica Scandinavica (1987), vol. 31, pp. 111–116.

Levy, W.J., "Quantitative analysis of EEG changes during hypothermia," Anesthesiology (1984), vol. 60, No. 4, pp. 291–297.

Bashein et al., "Electroencephalography during surgery with cardiopulmonary bypass and hypothermia," Anesthesiology (1992), vol. 76, No. 6, pp. 878–891.

Flaishon et al., "Detection of consciousness following thiopental: isolated forearm and bispectral EEG (BIS)," Anesthesiology (1995), vol. 83, No. 3A, A515.

Kearse et al. "The Bispectral Index correlates with sedation/hypnoses and recall: comparison using multiple agents," Anesthesiology (1995), vol. 83, No. 3A, A507.

Kearse et al., "Bispectral analysis of the electroencephalogram correlates with patient movement to skin incision during propofol/nitrous oxide anesthesia," Anesthesiology (1994), vol. 81, No. 6, pp. 1365–1370.

Vernon et al., "Prediction of movement using bispectral electroencephalographic analysis during propofol/alfentanil or isoflurane/alfentanil anesthesia," Anesthesia & Analgesia (1995), vol. 80, No. 4, pp. 780–785.

Thornton et al., "Effect of propofol on the auditory evoked response and oesophageal contractility," British Journal of Anaesthesia (1989), vol. 63, No. 4, pp. 411–417.

Davies et al., "Middle latency auditory evoked potentials during repeated transitions from consciousness to unconsciousness," Anaesthesia (1996), vol. 51, No. 1, pp. 107–113.

Newton et al., "Auditory evoked response and awareness: a study of volunteers at sub–MAC concentrations of isoflurane," British Journal of Anaesthesia (1992), vol. 69, No. 2, pp. 122–129.

Kenny et al., "Transition between consciousness and unconsciousness during anesthesia," Anesthesiology (1993), vol. 79, No. 3A, A330.

Kenny et al., "Closed–loop control of anesthesia," Anesthesiology (1992), vol. 77, No. 3A, A328.

Hett et al., "Effect of temperature and cardiopulmonary bypass on the auditory evoked response," British Journal of Anaesthesia (1995), vol. 75, pp. 293–296.

Kenny et al., "A portable target controlled propofol infusion system," International Journal of Clinical Monitoring and Computing (1992), vol. 9, No. 3, pp. 179–182.

Davies et al., "Postoperative analgesia using a computerized infusion of alfentanil following aortic bifurcation graft surgery," International Journal of Clinical Monitoring and Computing (1992), vol. 9, No. 4, pp. 207–212.

Markand et al., "Monitoring of multimodality evoked potentials during open heart surgery under hypothermia," Electroencephalography and Clinical Neurophysiology (1984), vol. 59, No. 6, pp. 432–440.

Blair, E., "A physiological classification of clinical hypothermia," Surgery (1965), vol. 58, No. 3, pp. 607–618.

Chassard et al., "Auditory evoked potentials during propofol anaesthesia in man," British Journal of Anaesthesia (1989), vol. 62, No. 5, pp. 522–526.

Leslie et al., "Propofol blood concentration and the Bispectral Index predict suppression of learning during propofol/epidural anesthesia in volunteers," Anesthesia & Analgesia (1995) vol. 81, No. 6, pp. 1269–1274.

Davidson et al., "Effective concentration 50 for propofol with and without 67% nitrous oxide," Acta Anaesthesiologica Scandinavica (1993), vol. 37, pp. 458–464.

Russell et al., "Propofol–fentanyl anaesthesia for coronary artery surgery and cardiopulmonary bypass," Anaesthesia (1989), vol. 44, No. 3, pp. 205–208.

Massey et al., "Pharmacokinetics of an infusion of propofol during cardiac surgery," British Journal of Anaesthesia (1990), vol. 65, No. 4, pp. 475–479.

Hynyen et al., "Propofol sequestration within the extracorporeal circuit," Canadian Journal of Anaesthesia (1994), vol. 41, No. 7, pp. 583–588.

Schwender et al., "Effects of increasing doses of alfentanil, fentanyl and morphine on mid–latency auditory evoked potentials," British Journal of Anaesthesia (1993), vol. 71, No. 5, pp. 622–628.

Jessop et al., "Evaluation of the actions of general anaesthetics in the human brain," General Pharmacology (1992), vol. 23, No. 6, pp. 927–935.

Jones, J.G., "Perception and memory during general anaesthesia," British Journal of Anaesthesia (1994), vol. 73, No. 1, pp. 31–37.

Sharpe et al., Auditory evoked response, median frequency and 95% spectral edge during anaesthesia with desflurane and nitrous oxide, British Journal of Anaesthesia (1997), vol. 78, pp. 282–285.

Kearse et al., "Bispectral analysis of the electroencephalogram during induction of anesthesia may predict hemodynamic responses to laryngoscopy and intubation," Electroencephalography & Clinical Neurophysiology (1994), vol. 90, No. 3, pp. 194–200.

Sebel et al., "EEG bispectrum predicts movement during thiopental/isoflurane anesthesia," Journal of Clinical Monitoring (1995), vol. 11, No. 2, pp. 83–91.

Liu et al., "Electroencephalogram bispectral analysis predicts the depth of midazolam–induced sedation," Anesthesiology (1996), vol. 84, No. 1, pp. 64–69.

Kenny et al., "Validation of monitoring anesthetic depth by closed–loop control. In: Memory and Awareness in Anesthesia," Sebel P. Bonke, Winograd E. eds. Prentice Hall, Englewood Cliffs (1993), pp. 255–264.

Levy et al., "Automated EEG processing for intraoperative monitoring: a comparison of techniques," Anesthesiology (1980), vol. 53, No. 3, pp. 223–236.

Sigl et al., "An introduction to bispectral analysis for the electroencephalogram," Journal of Clinical Monitoring (1994), vol. 10, No. 6, pp. 392–404.

Howell et al., "Defining the $CP_{50}$ and $BIS_{50}$ for propofol alone and propofol with alfentanil," Anesthesiology (1995), vol. 83, No. 1, A367.

Russell, I.F., "Midazolam–alfentanil: an anaesthetic? An investigation using the isolated forearm technique," British Journal of Anaesthesia (1993), vol. 70, No. 1, pp. 42–46.

Lambrechts et al., "Postoperative amnesia," British Journal of Anaesthesia (1961), vol. 33, No. 8, pp. 397–404.

Artusio, J.F. Jr., "Ether analgesia during major surgery," Journal of the American Medical Association (1955), vol. 157, No. 1, pp. 33–36.

Rupreht, J., "Awareness with amnesia during total intravenous anaesthesia with propofol (letter)," Anaesthesia (1989), vol. 44, No. 12, p. 1005.

Sawtelle et al., "Bispectral EEG index predicts awakening," Anesthesiology (1994), vol. 81, No. 3A, A213.

Gajraj et al., "A comparison of auditory evoked potentials and bispectral EEG analysis in spontaneously breathing anesthetized patients," Anesthesiology (1996), vol. 85, No. 3A, A462.

Schwilden et al., "Quantitative EEG analysis during anaesthesia with isoflurane in nitrous oxide at 1.3 and 1.5 MAC," British Journal of Anaesthesia (1987), vol. 59, No. 6, pp. 738–745.

Schwilden et al., "Closed–loop feedback control of methohexital anesthesia by quantitative EEG analysis in humans," Anesthesiology (1987), vol. 67, No. 3, pp. 341–347.

Schwilden et al., "Quantitation of the EEG and pharmacodynamic modeling of hypnotic drugs: etomidate as an example," European Journal of Anaesthesiology (1995), vol. 2, No. 2, pp. 121–131.

Levy, W.I., "Intraoperative EEG patterns: implications for EEG monitoring," Anesthesiology (1984), vol. 60, No. 5, pp. 430–434.

Liu et al., "Incidence of awareness with recall during general anesthesia," Anaesthesia (1991), vol. 46, No. 6, pp. 435–437.

Arndt et al., "EEC–Veranderungen unter Propofol–Alfetanil–Lachgas–Naekoaw," [EEG changes during propofol–alfentanil–nitrous oxide anesthesia] [German] (1995), vol. 20, pp. 126–133.

Clark et al., "Neurophysiologic effects of general anesthetics: I. The electroencephalogram and sensory evoked responses in man," Anesthesiology (1973), vol. 38, No. 6, pp. 564–582.

Rosner et al., "Neurophysiologic effects of general anesthetics: II Sequential regional actions in the brain," Anesthesiology (1973), vol. 39, No. 1, pp. 59–81.

Vernon et al., "EEG bispectrum predicts movement at incision during isoflurane or propofol anesthesia," Anesthesiology (1992), vol. 77, No. 3A, A502.

Glass et al., "Quantification of the relative effects of anesthetics agents on the EEG and patient responsiveness to incision," Anesthesiology (1994), vol. 81, No. 3A, A407.

Lang et al., "Bispectral EEG analysis, analgesia and movement at incision during propofol/alfentanil/N20 anesthesia," Anesthesiology (1994), vol. 81, No. 3A, A476.

Sebel et al., "Bispectral analysis (BIS) for monitoring anesthesia: comparison of anesthetic techniques," Anesthesiology (1994), vol. 81, No. 3A, A1488.

Thornton et al., "Effects of halothane or enflurane with controlled ventilation on auditory evoked potentials," British Journal of Anaesthesia (1984), vol. 56, No. 4, pp. 315–323.

Thornton et al., Effect of etomidate on the auditory evoked response in man, British Journal of Anaesthesia (1985), vol. 57, No. 6, pp. 554–561.

Heneghan et al., "Effect of isoflurane on the auditory evoked response in man" British Journal of Anaesthesia (1987), vol. 59, No. 3, pp. 277–282.

de Beer et al., "Haemodynamic responses to incision and sternotomy in relation to the auditory evoked potential and spontaneous EEG," British Journal of Anaesthesia (1996), vol. 76, No. 5, pp. 685–693.

Thornton et al., "Effects of surgical stimulation on the auditory evoked response," British Journal of Anaesthesia (1988), vol. 60, No. 4, pp. 372–378.

Schwender et al., "Effects of surgical stimulation on midlatency auditory evoked potentials during general anaesthesia with propofol/fentanyl, isoflurane/fentanyl and flunitrazepam/fentanyl," Anaesthesia (1994), vol. 49, No. 7, pp. 572–578.

Sebel et al., "Bispectral analysis for monitoring anesthesia—a multicenter study," Anesthesiology (1993), vol. 79, No. 3A, A178.

Thornton et al., "Enflurane anaesthesia causes graded changes in the brainstem and early cortical auditory evoked response in man," British Journal of Anaesthesia (1983), vol. 55, No. 6, pp. 479–486.

Thornton et al., "Selective effect of althesin on the auditory evoked response in man," British Journal of Anaesthesia (1986), vol. 58, No. 4, pp. 422–427.

Goldstein et al., "Effects of stimulus rate and number on the early components of the averaged electroencephalographic response," Journal of Speech and Hearing Research (1972), vol. 15, No. 3, pp. 559–566.

McFarland et al., "Reexamination of effects of stimulus rate and number on the middle components of the averaged electroencephalographic response," Audiology (1975), vol. 14, pp/ 456–465.

Thornton et al., "The auditory evoked response: a measure of depth of anaesthesia," Bailliere's Clinical Anesthesiology (1989), vol. 3, No. 3, pp. 559–585.

Sebel et al., Evoked responses—a neurophysiological indicator of depth of anaesthesia? (editorial), British Journal of Anaesthesia (1985), vol. 57, No. 9, pp. 841–842.

Thornton, C., "Evoked potentials in anaesthesia," European Journal of Anaesthesiology (1991), vol. 8, pp. 89–107.

Madler et al., "Auditory evoked potentials indicate the loss of neuronal oscillations during general anaesthesia," Naturwissenschaften (1987), vol. 74, pp. 42–43.

Madler et al., "Sensory information processing during general anaesthesia: effect of isoflurane on auditory evoked neuronal oscillations," British Journal of Anaesthesia (1991), vol. 66, No. 1, pp. 81–87.

Schwender et al., "Mid–latency auditory evoked potentials during ketamine anaesthesia in humans," British Journal of Anaesthesia (1993), vol. 71, No. 5, pp. 629–632.

Schwender et al., "Motor signs of wakefulness during general anaesthesia with propofol, isoflurane and flunitrazepam/fentanyl and midlatency auditory evoked potentials," Anesthesia (1994), vol. 49, No. 6, pp. 476–484.

Thornton et al., "The auditory evoked response as an indicator of awareness," British Journal of Anaesthesia (1989), vol. 63, No. 1, pp. 113–115.

* cited by examiner

ANAESTHESIA CONTROL SYSTEM

This application is a continuation of U.S. Ser. 09/267,932, filed Mar. 11, 1999, entitled Anaesthesia Control System, now abandoned, which is a continuation of PCT International Application No. PCT/GB97/02435, filed Sep. 10, 1997, entitled Anaesthesia Control System, and claims the benefit of Great Britain Application Serial No. 9618998.0, filed Sep. 11, 1996, assigned to the assignee of the present application, the disclosures of which are hereby incorporated herein by reference in their entirety as if set forth fully herein.

The present invention relates to an anaesthesia control system and a method for calculating an index representative of the depth of anaesthesia. The invention is applicable in particular, though not exclusively, to a system and method for providing closed-loop anaesthesia control such as will safely maintain a patient in an unconscious state without requiring human intervention.

Conventional anaesthesia systems require an anaesthetist to manually control the anaesthetic dose given to a patient in dependence upon displayed vital signs, e.g. heart rate and blood pressure, and upon the visually observable reaction of the patient. However, when a patient is paralysed and ventilated these vital signs are not completely reliable as indicators of anaesthesia depth and there have been reports of patients being awake during an operation despite their vital signs being within normal limits.

In an attempt to eliminate or reduce the possibility for error in the dosage of an anaesthetic, research has been carried out into providing a more reliable indication of anaesthesia depth and, in particular, a more direct index of anaesthesia depth. Almost all proposals have relied upon the analysis of cerebral electrical activity and more particularly of recorded electroencephalographic (EEG) signals.

The cerebral function analysis monitor (CFAM) [see Sebel P S, Maynard D E, Major E, Frank M, "The Cebrel Function Analysis Monitor (CFAM): A New Microprocessor-based Device for the On-line Analysis of the EEG and Evoked Potentials", BR J Anaesth 1983; 55: 1265–1270] is a commercially available system which provides a quantitative indication of anaesthetic depth. The CFAM system functions by analysing the spectrum of recorded EEG signals.

In an attempt to establish a more reliable method for measuring depth of anaesthesia, researchers have recently investigated the change in lower oesophageal contractility associated with anaesthesia. This contractility has been shown to be related to the end-tidal concentration of volatile anaesthetics. However, it has been found that this method is insufficiently discriminating at the interface between consciousness and unconsciousness to be used as a monitor of anaesthetic depth.

Despite the considerable amount of research carried out in this area, the anaesthesia indices obtained by researchers remain unreliable and there exists considerable reluctance to allow the widespread introduction of closed-loop anaesthesia control systems. WO 93/07804 describes a system in which a quantitative measure of anaesthetic depth is again obtained by analysing the frequency spectrum of the recorded signals. A system implementing this approach is the 'A1000'™ monitor available from Aspect Medical Systems, Inc. Massachusettes, USA.

It is an object of the present invention to overcome or at least mitigate certain of the disadvantages of the above systems and methods.

In particular, it is an object of the present invention to provide a system and method for generating a reliable quantitative measure of anaesthetic depth.

It is a further object of the present invention to provide an anaesthesia index which is a measure of anaesthetic depth and which may be used in a closed-loop anaesthesia control system.

According to a first aspect of the present invention there is provided a method of calculating an index indicative of anaesthetic depth, the method comprising subjecting a patient to a repetitive audio stimulus, monitoring auditory evoked potentials (AEP) produced by the patient, and providing a signal corresponding to the coarseness of the monitored AEP signal, and using said signal as said index indicative of anaesthetic depth.

It has been found that the coarseness of the AEP signal provides a good indication of anaesthesia depth, with the coarseness of the signal being found to decrease as the depth of anaesthetic increases.

The term 'coarseness' is used here to means a combined measure of the amplitude and frequency of the monitored AEP signal i.e. a measure of the curvature of the signal. Typically, a high coarseness equates to a signal having large amplitude and high frequency whilst a low coarseness equates to a signal having low amplitude and low frequency. Intermediate 'coarseness' may be a low amplitude/high frequency or a high amplitude/low frequency. It will be appreciated that it is difficult to give an absolute specification or definition of coarseness; coarseness is a relative measurement of a time varying signal which varies in amplitude and in frequency. The term coarseness is used to define a parameter which can be readily used in the implementation of the method and apparatus in the clinical environment.

In a preferred embodiment of the present invention, the monitored or raw AEP signal is divided into a series of sweeps or frames of a given duration, each sweep being synchronised with the repetitive audio stimulus. A number of sweeps n are recorded in sequence and are averaged to produce a time averaged sweep. For the time averaged sweep the anaesthesia index is calculated. Each time a new series of sweeps is recorded, a new time averaged sweep is determined from the most recent n sweeps and the anaesthesia index for that time averaged sweep calculated. In this way the anaesthesia index is constantly updated.

Where the method involves the use of a digital computer, the raw AEP signal is sampled at regular intervals to produce a digitised AEP signal. A preferred method of obtaining said indication of coarseness is to obtain a measure of the differences between neighbouring sample points. In the case where a moving time averaged sweep is obtained, this measure may be a function of the sum of the square roots of the difference between every two adjacent sample points in the time averaged sweep.

According to a second aspect of the present invention there is provided a method of maintaining closed-loop control of anaesthesia depth, the method comprising supplying a dosage of anaesthetic to a patient, calculating an anaesthetic depth index according to the above first aspect of the present invention, and using the value of the anaesthetic depth index to regulate the anaesthetic supply to maintain the anaesthesia depth index at or near a predetermined level.

According to a third aspect of the present invention there is provided a system for calculating an index of anaesthetic depth, the system comprising a signal generator for subjecting a patient to a repetitive audio stimulus, electroencephalographic (EEG) recording means for coupling to said patient for recording auditory evoked potential (AEP) signal from the patient, and computer means for receiving said AEP signal, and for processing said AEP signals and generating an index signal indicative of the coarseness of the recorded AEP signal, said index signal being representative of the depth of anaesthesia.

According to a fourth aspect of the present invention there is provided an anaesthetic supply control system including a system for calculating an index of anaesthetic depth according to the above third aspect of the present invention for a patient, and anaesthetic supply means including a regulator for regulating the supply of anaesthetic to the patient to maintain the anaesthetic depth index at a predetermined level.

The present invention is particularly applicable to anaesthesia systems which use a liquid anaesthetic, such as propofol, the dosage of which can be very accurately regulated.

For a better understanding of the present invention and in order to show how the same may be carried into effect reference will now be made, by way of example, to the accompanying drawings in which.

Figure 1:
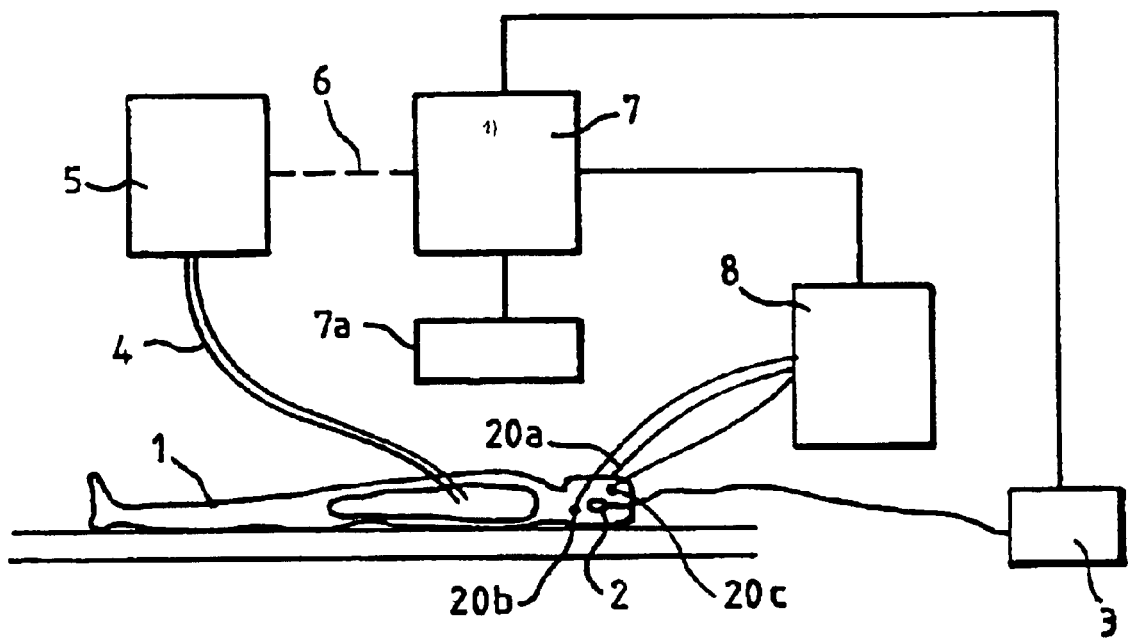
FIG. 1 shows schematically an embodiment of an anaesthesia control system according to the present invention.

There is shown in FIG. 1 an anaesthesia control system for maintaining a patient 1 in an unconscious state whilst the patient undergoes surgery. The patient 1 wears a pair of earphones 2 which are driven by a signal generator 3 to sound "clicks" of 1 ms duration at a frequency of 6.9 Hz to both the patient's ears. The amplitude level of the clicks is maintained at 70 dB above normal hearing level. It is well known in the field of neurophysiology that such repetitive clicks sounded in the ears of a patient will produce distinctive potentials, known as auditory evoked potentials (AEP), in the electroencephalographic (EEG) response of the patient. [See Kenny G N, Davies F W, Mantzaridis H. "Transition between consciousness and unconsciousness during anesthesia". *Anesthesiology* 1993; 79: A330 and Kenny G N, Davies F W, Mantzaridis H, Fisher A C. "Closed-loop control of anesthesia". *Anesthesiology* 1992; 77: A328].

A liquid anaesthetic, for example propofol, is supplied intravenously to the patient through a tube 4 from a pump 5. The pump is of a known type (e.g. Ohmeda 9000™ syringe pump) which is controlled to accurately regulate the anaesthetic dose given to the patient. A controller 7 is arranged to process AEP signals for the purpose of generating an anaesthetic depth index for display on a controller display 7a. The anaesthetist uses the displayed index to control the pump 5.

Figure 2:
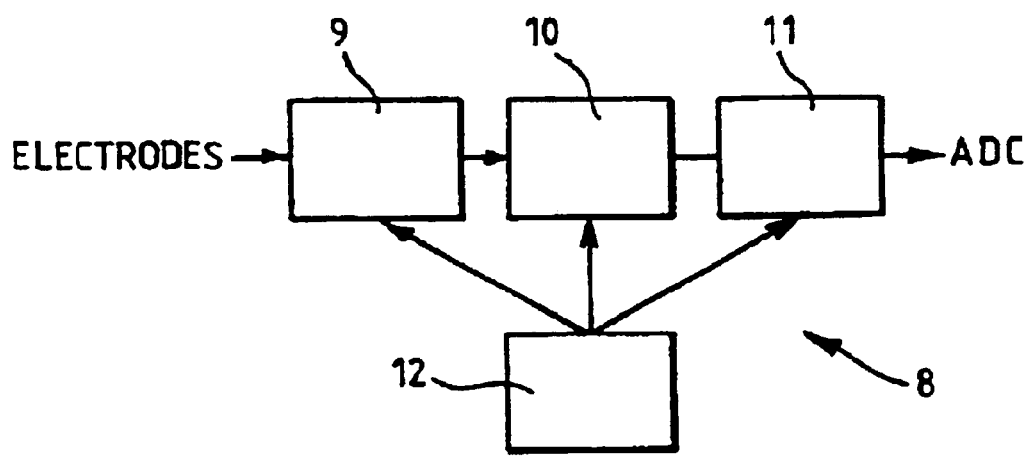
FIG. 2 is a block diagram of the EEG amplifier of the system of FIG. 1.

The controller 7 receives an analogue input signal from an EEG amplifier 8 which is shown in greater detail in FIG. 2. The EEG amplifier 8 comprises at its input a medical grade preamplifier 9 the output of which is fed to a main amplifier 10. Power is supplied to the EEG amplifier components from a power supply 12. The main requirements of the EEG amplifier 8 are:

1) A very high common mode rejection ratio (CMRR), typically in excess of 110 dB, even when the electrode impedances are not matched;
2) A frequency response in the range 1 to 300 Hz;
3) The amplifier should be portable with small physical dimensions;
4) The system should be suitable for theatre use, i.e. with shielded or guarded leads, appropriate patient isolation, immunity to diathermy and other sources of interference.

Figure 3:
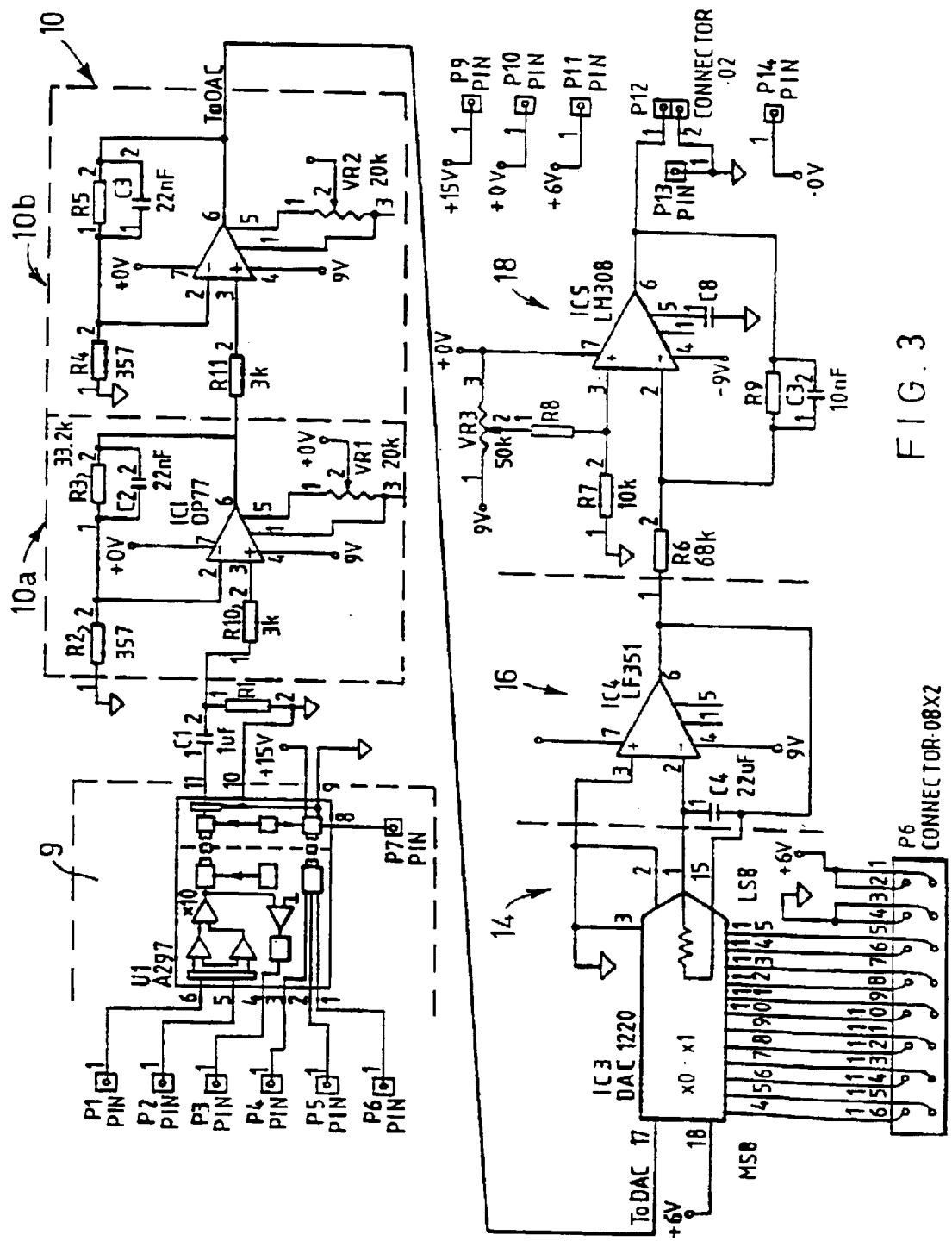
FIG. 3 shows a detailed circuit diagram for the EEG amplifier of FIG. 2.

FIG. 3 shows in greater detail the circuitry comprising the EEG amplifier 8. The preamplifier 9 is provided by an IA 297 medical grade isolation amplifier (Intronics, USA) which provides full patient protection from leakage currents and amplifier fault currents. This applies to both input protection and input/output isolation currents. The IA 297 is an ultra low noise true medical isolation amplifier which can operate at common mode input voltages of up to 5000V DC continuous. The common mode rejection ratio (CMRR) is 170 dB with a balanced source impedance and 160 dB with a 5KΩ source imbalance. The input noise voltage of the preamplifier is 0.3 $\mu$V (10 Hz to 1 kHz rms) and the current noise is 4 pA (0.05 Hz to 1 kHz rms). The input bias current is 200 pA and is limited to 10 $\mu$A in the event of failure of any component. The frequency response of the preamplifier is from DC to 10 KHz and the overload recovery time is 20 ms. The IA 297 provides an overall gain of ×10.

The output from the preamplifier U1 is filtered by the high-pass filter network C1-R1 which provides a −3 dB cut-off point at 0.9 Hz. The filtered signal is then amplified by two identical amplification stages 10a, 10b arranged in series. Each amplification stage 10a, 10b is based around an operational amplifier (OP77) which offers exceptional gain linearity with an equivalent input noise of 10 0nV/√Hz. The gain of each amplification stage 10a, 10b is ×94 to give an overall amplifier gain at the output of the second amplification stage of 88360 (10×94×94).

The output from the second amplification stage 10b is supplied to a digital attenuator comprising a 12 bit digital-to-analogue converter 14 based on IC3 which is a DAC 1220 has a linearity error of 0.05% fullscale. This error is substantially independent of the voltage reference. The output from the attenuator is supplied to a wide bandwidth JFET operational amplifier (IC4) 16, which has an input bias current of 50 pA and an equivalent input noise of 25 nV/√Hz and which acts as a buffer amplifier having a gain of ×1.

The output stage of the EEG amplifier 8 consists of a further ×1 gain amplifier 18 (IC5) which allows a DC offset to be introduced to the amplified signal. This offset simplifies the connection to subsequent unipolar analogue to digital converters.

At intermediate points in the EEG amplifier 8, the signal is filtered by three low-pass first order filters (C2-R3, C3-R5 and C5-R9) which each have a −3 db cut-off point at 219 Hz.

All of the resistors used in the EEG amplifier 8 are precision metal film resistors with a 0.1% tolerance and a temperature coefficient of ±15 ppm/° C. The polarised capacitors of the amplifier 8 are solid tantalum and the non-polarised capacitors are metallised polycarbonate film with 5% tolerance and a temperature coefficient of ±50 ppm/° C. Ceramic bypass capacitors are used to reduce instabilities caused by transients in the power supply lines.

The power supply unit for the EEG amplifier is of a conventional linear AC/DC design which provides high stability, low noise outputs of +15V, ±9V and +5V for the various stages of the amplifier. It also offers 5000V isolation between its primary and secondary coils. Power supplies having these characteristics are commercially available from, for example, 'RS', 'Amplicon', or 'Tandy' (all TMs).

The EEG amplifier 8 is situated as close as possible to the head of the patient and is coupled to three electrodes 20 attached to the patient's head. A first electrode 20a is placed on the right forehead (+), a second electrode 20b is placed on the right mastoid (−), and the third electrode 20c is placed on the middle of the forehead (references. It has been found that standard disposable ECG electrodes (for example M-00-S by Medicotest) provide acceptable results provided that the patient's skin is carefully cleaned with alcohol swabs prior to attaching the electrodes with electrode jelly.

There are two very important reasons for ensuring that the electrode/skin impedances of the electrodes are as low as possible. Firstly, thermal or Johnson noise is generated by the electrode/skin resistance and is proportional to the square root of the resistance. Secondly, the CMRR is reduced significantly if the electrodes have imbalanced impedances. The balancing of the impedances is easier to achieve if the impedances are as low as possible.

More recently, a new type of electrode, known as "Zipprep"™ (produced by Aspect Medical Systems), has become available. These electrodes achieve very low impedances with minimal skin preparation and are suitable for use with the system described herein.

With reference to FIG. 1, the controller 7 is used to trigger the signal generator 3 to sound repeated clicks in the patient's right ear. Synchronisation of the signal generator is important in ensuring that the is anaesthesia index, calculated as described hereinbelow, is as reliable as possible.

The physical construction of the microprocessor based controller 7 will not be set out in detail here as it is a standard design. Indeed, whilst it may be preferable to design a purpose built controller in order to achieve a more portable and cost efficient design, the controller is readily implemented by a standard desktop or notebook personal computer.

Before describing the structure of the control program, the method used to calculate an index of anaesthesia depth will now be described.

Figure 4:
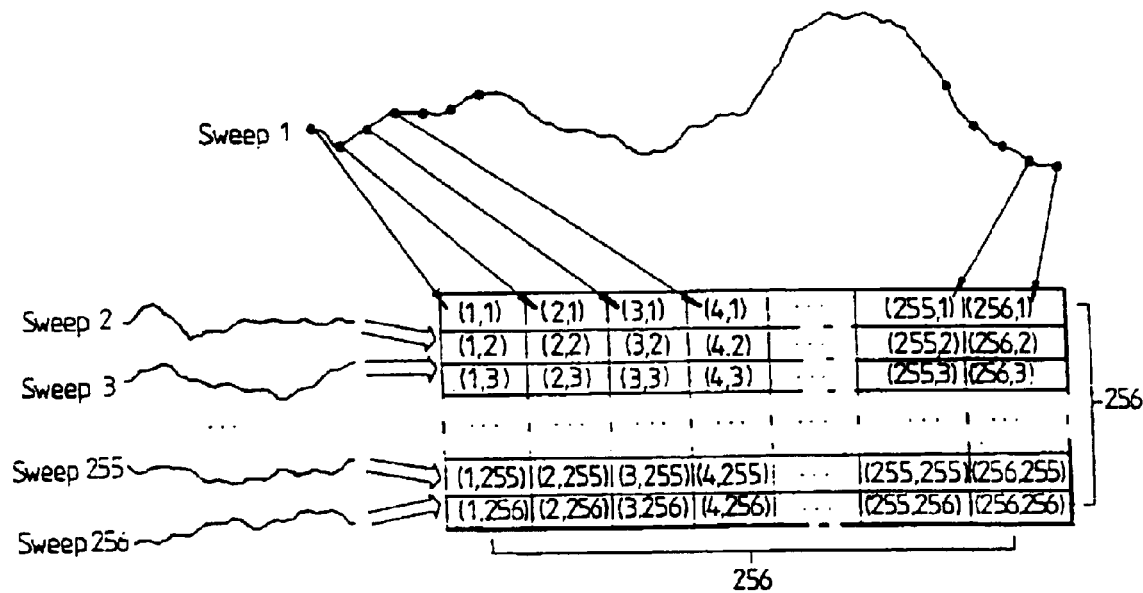
FIG. 4 illustrates schematically the collection of 256 consecutive AEP frames using the system of FIG. 1.

In order to calculate the anaesthetic depth index, a recorded EEG signal is sampled at a rate of 1.7 KHz by a 12 bit analogue to digital converter (PCM-DAS08, Computer Boards Inc. MA., U.S.A.) and was processed in realtime by the computer. These samples are buffered in "sweeps" of 256 samples such that each sweep extends over a duration of 144 ms. Auditory evoked potentials were produced by averaging these sweeps. As illustrated in FIG. 4, a memory table of the controller 7 is created to store 256 consecutive sweeps. When a first group of 256 sweeps have been recorded, an averaged AEP curve or sweep is generated by averaging the 256 sweeps, i.e. by averaging the recorded 256 samples in each column of the memory table as illustrated in FIG. 5.

Figure 5:
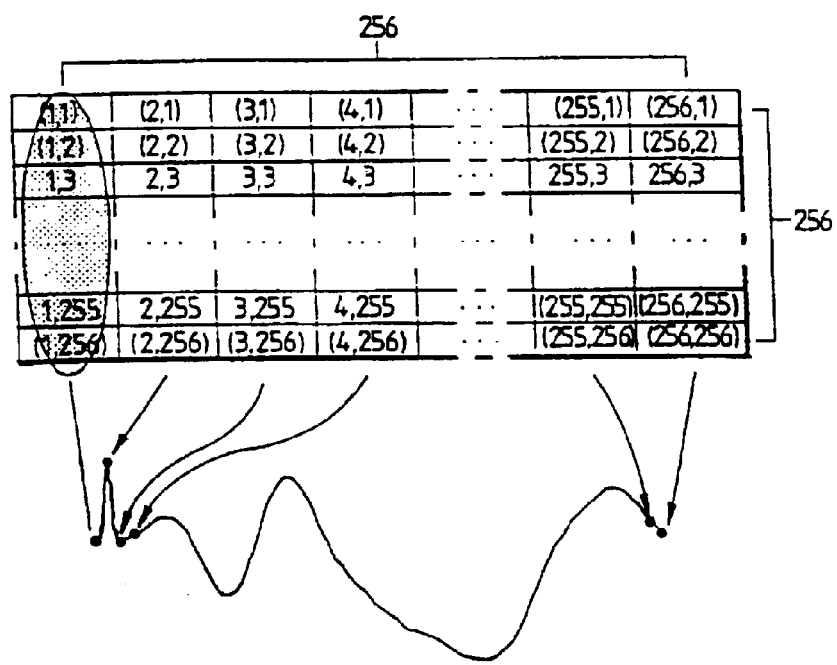
FIG. 5 illustrates a schematically moving time averaged frame obtained from the 256 consecutive frames of FIG. 4.

Each time a new 256 sample sweep is recorded, the memory table shown in FIGS. 4 and 5 is updated by discarding the sweep at the top of the table i.e. sweep 1, and adding the new sweep to bottom of the table, i.e. as new sweep 256. A new time averaged sweep is then generated so that over a period of time a sequence of moving time averaged sweeps are created. This technique allows a faster response of the system to changes in the AEP signals.

A common source of error in AEP signals is due to artefacts which arise mainly from patient or electrode movement and the use of diathermy during surgery. Each newly recorded sweep is therefore examined to see if the signal amplitude at any point in the sweep exceeds a preset limit. If this limit is exceeded, the sweep is rejected and is not added to the table of FIG. 4. Typically, several subsequent sweeps (for example seven) following a sweep detected as containing an artifact are rejected before sweeps are once again added to the table of FIGS. 4 and 5. In order to further enhance the time averaged sweeps, these sweeps are filtered by a digital low-pass finite impulse response (FIR) filter. The frequency response of this filter is 0–0.049 of the Nyquist interval. The filter is a 35 point filter (18 coefficients) having a raised cosine window.

The FIR filter is described by the difference equation:

$$y(n) = \sum_{k=0}^{M-1} b_k x(n-k)$$

Where x(n) is the input to the filter, y(n) is the output, M is the number of coefficients (in this case 35), and $b_k$ are the coefficients.

FIR filters have a number of advantages including their linear phase response and their high level of stability which results from the absence of feedback.

Once a moving time averaged and filtered frame has been obtained as described above, it is possible to calculate an index of anaesthesia depth. It has been observed that when patients lose consciousness, the amplitudes of most AEP peaks are reduced and their latencies are generally also increased. These changes occur almost simultaneously, and in the same direction, with all patients. A suitable index therefore is one which reflects these changes.

An empirical algorithm has been developed for calculating such an index and is based upon the sum of the square roots of the difference between every two successive points in the moving time averaged sweep. This auditory evoked potential index is given by the following equation:

$$AEP = k \sum_{i=1}^{255} \sqrt{|x_i - X_{i+1}|}$$

Where $x_1$ to $x_{256}$ are the sample points of the time averaged frame and k is a scaling constant equal to $0.25 \times \sqrt{V^{-1}}$.

The AEP index is calculated for every filtered time averaged sweep and a plot of the index against time can be generated by the controller 7 for display on the controller display 7a. When the patient is awake the index is typically in the range 80 to 90 whereas during anaesthesia it is typically in the range 35 to 40. When the patient recovers consciousness, the index usually returns to a value slightly lower than the value immediately prior to anaesthesia.

Figure 6:
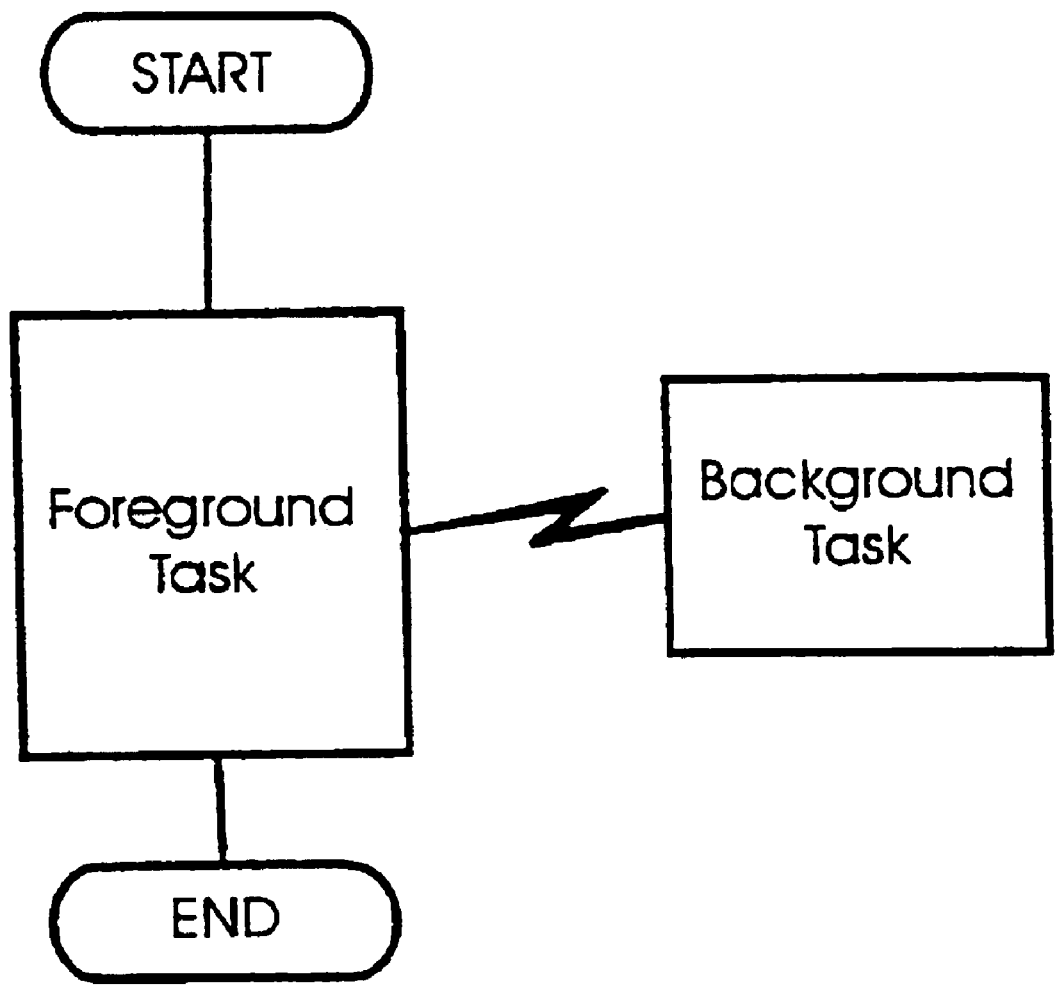
FIG. 6 shows the general organisation of software used to control a microprocessor of the system of FIG. 1.

FIG. 6 shows in general terms the organisation of the controller software which implements the algorithm described above for calculating the AEP index as a measure of anaesthetic depth. The program has a multi-tasking organisation with a foreground task and a background task running parallel to one another. These tasks are completely independent and communicate through "semaphores". The foreground task acts as an interface between the user and the background task causing the background task to initialise, start and stop.

Figure 7:
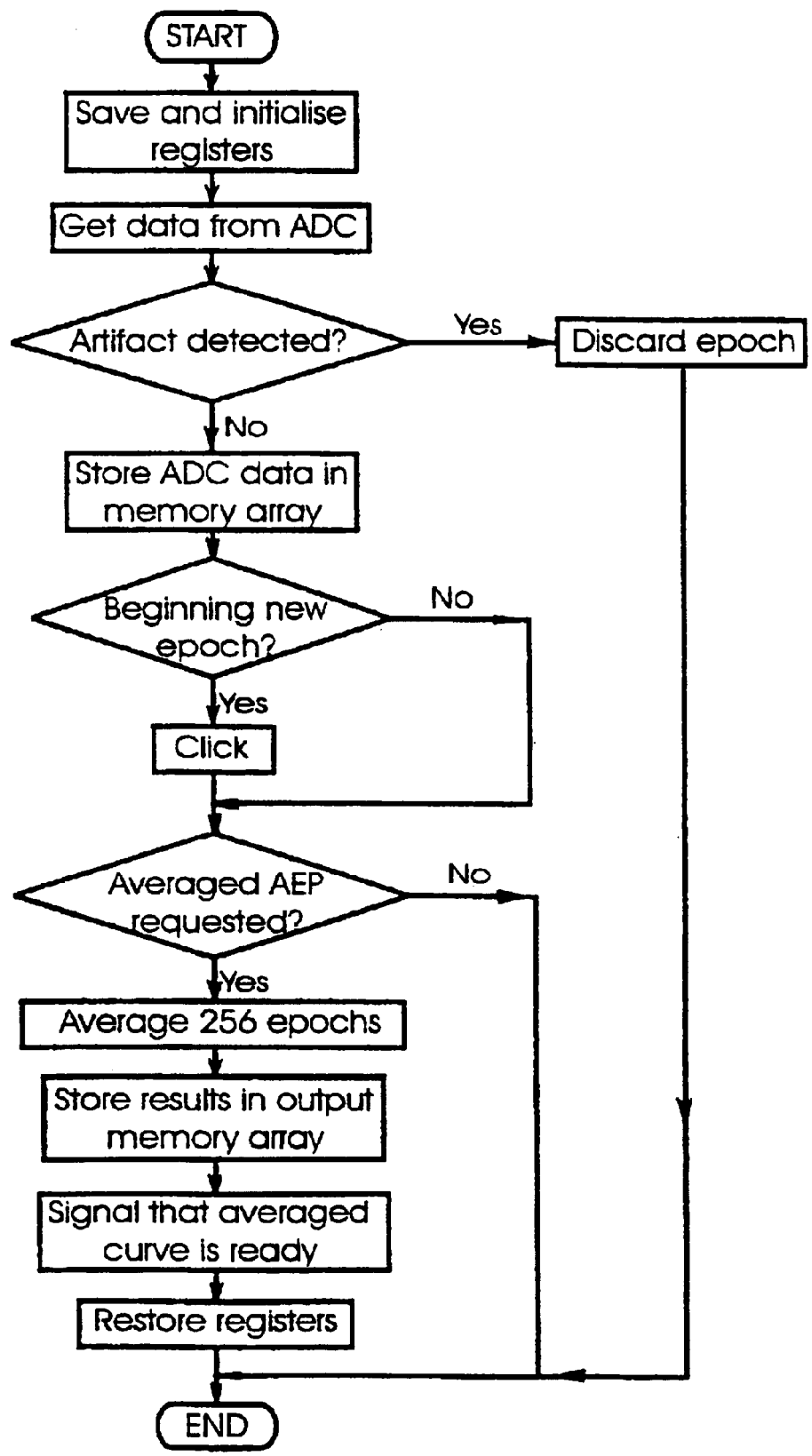
FIG. 7 is a flow chart of a background task of the software of FIG. 6.

FIG. 7 shows in more detail the methodology of the background task. The recorded EEG signal is received by an analogue to digital converter of the controller (not shown) which, for sweeps consisting of 256 samples and with a duration of 144 ms, generates hardware interrupts at a rate of 1.78 KHz. These hardware interrupts cause the background task to read the data currently on the output of the ADC. In one cycle of the background task, from "start" to "end", a new single sample point is added to the memory table. If an artefact is detected as being present in a given sweep, that sweep is discarded. At the beginning of each new sweep, a further click is generated in order to ensure correct synchronisation of the subsequently generated sweep with the click. When the last point in each sweep is obtained, a new moving time averaged frame is calculated.

Figure 8:
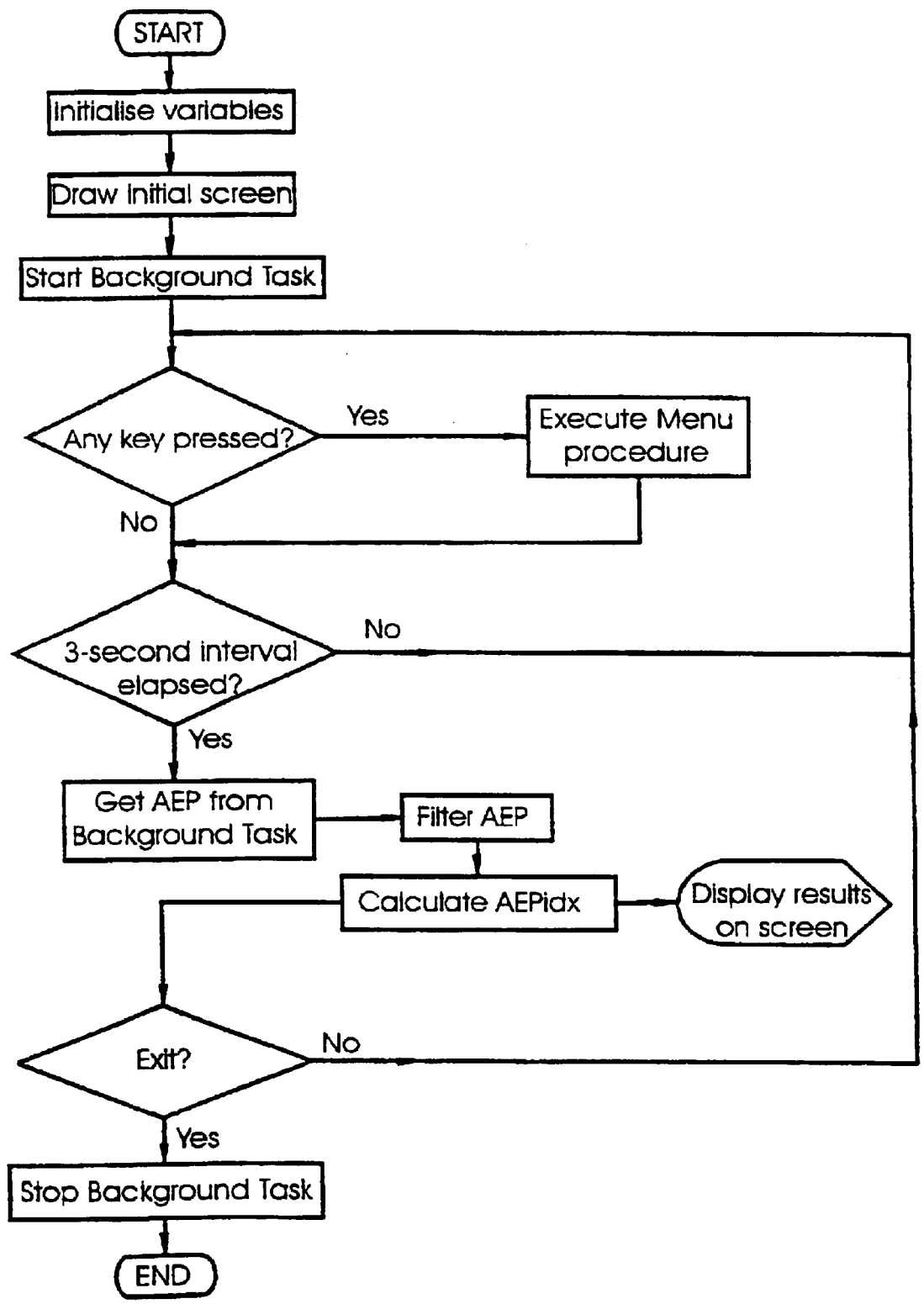
FIG. 8 is a flow chart of a foreground task of the software FIG. 6.

FIG. 8 shows the general structure of the foreground task which interfaces the user to the background task. Once the foreground task is initialised, and has initialised and started the background task, it obtains the most recently generated time averaged AEP sweep from the background task. This AEP sweep is filtered using the FIR filter described above and the anaesthesia depth index calculated as discussed. The index is displayed on the controller display 7a for viewing by the anaesthetist.

It will be appreciated by the skilled person that various modifications may be made to the above described embodiment without departing from the scope of the invention. In particular the system may be made into a closed loop anaesthesia control system by providing a control output, corresponding to the determined anaesthetic depth index, from the controller 7 to the pump 5. Thus is indicated in FIG. 1 by the dotted line 6.

The system has been used clinically and is the subject of several studies: "Relationship between calculated blood concentration of propofol and electrophysiological variables during emergence from anaesthesia: comparison of bispectral index, spectral edge frequency, median frequency and auditory evoked potential index": M. Doi, R. J. Gajraj, H. Mantzaridis and G. N. C. Kenny, *British Journal of Anaesthesia*, February 1997, Vol 78, No 2, p180–184: and "Effects of Cardiopulmonary Bypass and Hypothermia on Electroencephalographic Variables": M. Doi, R. J. Gajraj, H. Mantzaridis, and G. N. C. Kenny, (Accepted for Publication in 'Anaesthesia') [See Appendix 1]; "Analysis of the EEG bispectrum, auditory evoked potentials and the EEG power spectrum during repeated transitions from consciousness to unconsciousness": R. J. Gajraj, M. Doi, H. Mantzaridis and G. N. C. Kenny, (Accepted for publication in '*British Journal of Anaesthesia*') [See Appendix 2]; "Auditory Evoked Potential Index: A Quantitative Measure of Changes in Auditory Evoked Potentials during General Anaesthesia": H. Mantzaridis and G. N. C. Kenny, (Accepted for publication in 'Anaesthesia') [See Appendix 3].

WO 98/10701 — 14 — PCT/GB97/02435

Professor GNC Kenny.
University Department of Anaesthesia,
Royal Infirmary, 8-16 Alexandra Parade, Glasgow G31 2ER

APPENDIX 1

EFFECTS OF CARDIOPULMONARY BYPASS AND HYPOTHERMIA ON ELECTROENCEPHALOGRAHIC VARIABLES

M. DOI, R.J. GAJRAJ, H. MANTZARIDIS, AND G.N.C. KENNY

---

Matsuyuki Doi, MD; Research fellow*

Roger J. Gajraj, FRCA; Research fellow*

Haralambos Mantzaridis, PhD, MB ChB; Senior house officer**

Gavin N.C. Kenny, FRCA; Professor and Head ***

* Department of Anaesthesia,

HCI International Medical Centre, Clydebank G81 4HX, U.K.

** Department of Anaesthetics, Law Hospital, Carluke, Lanarkshire ML8 5ER, U.K.

*** University Department of Anaesthesia, Royal Infirmary, 8-16 Alexandra Parade, Glasgow G31 2ER, U.K.

Correspondence should be addressed to Professor GNC Kenny.

University Department of Anaesthesia, Royal Infirmary, 8-16 Alexandra Parade, Glasgow G31 2ER U.K.

SUBSTITUTE SHEET (RULE 26)

SUMMARY

We studied the effects of hypothermia and cardiopulmonary bypass (CPB) on four depth of anaesthesia monitors: spectral edge frequency (SEF), median frequency (MF), Bispectral Index (BIS) and Auditory Evoked Potential Index (AEPIndex) in twelve patients during uneventful cardiac anaesthesia. Each variable was recorded simultaneously at 10 periods during anaesthesia. All four variables were not affected by the transition to CPB. During hypothermia, values of AEPIndex, MF and SEF were tightly distributed but values of BIS were very variable and overlapped with those before induction of anaesthesia. The variability decreased during rewarming. The values of AEPIndex throughout the anaesthesia never overlapped with those before induction of anaesthesia. The AEPIndex was the most stable and reliable as a depth of anaesthesia monitor among the four variables in cardiac bypass surgery.

Key words: Auditory Evoked Potential Index, Auditory evoked potential, Bispectral Index, Median frequency, 95% Spectral edge frequency, Cardiopulmonary bypass, hypothermia Running title: Effects of CPB and hypothermia on EEG

INTRODUCTION

Awareness is a particular problem in cardiac anaesthesia with cardiopulmonary bypass (CPB). Electrophysiological methods are possible candidates to quantify depth of anaesthesia and to detect awareness during anaesthesia. For clinical purpose, the electrophysiological activity should be provided continually in a format that can be easily evaluated, for example a single numerical value. When electrophysiological methods are used as an intraoperative monitoring tool during hypothermia, temperature-dependent effects must be clearly defined [1].

Several investigations have shown that derivatives of surface electroencephalogram reflected the depth of anaesthesia. Among them, spectral edge frequency (SEF)[2],[3],[4],[5] and median frequency (MF)[5],[6] have been studied as the single numerical parameter. Although temperature dependent changes of SEF [7], [8], [9] and MF [9] have been studied, their results were inconsistent and there was no study under anaesthesia with propofol and alfentanil. Recently bispectral analysis of EEG has provided a new variable, the Bispectral Index (BIS). Although BIS has been shown to detect consciousness [10][11] and to predict movement in response to surgery [12][13], effects of CPB or hypothermia on the BIS have not been reported.

Auditory evoked potentials (AEP) is another possible monitor of the depth of anaesthesia. Middle latency auditory evoked potential (MLAEP) has been reported to correlate well with anaesthetic depth [14] and to be able to demonstrate potential awareness [15],[16]. However, the MLAEP are usually obtained intermittently and the waveforms are difficult to use in the clinical situation. More recently, the Auditory Evoked Potential Index (AEPIndex; formerly knows as the Level of Arousal Score) was derived from AEP and has been proposed as a single numerical value for anaesthetic depth monitoring [17],[18],[19],[20]. The AEPIndex reflects the morphology of AEP waveforms and is calculated from the amplitude difference between successive segments of the curve [19],[20]. Although Hett and the colleagues [21] reported the effect of hypothermia and CPB on AEP, changes of AEPIndex during cardiac anaesthesia have not been reported.

We simultaneously recorded the four variables; AEPIndex, BIS, SEF and MF, from patients undergoing uneventful cardiac bypass surgery. The aim of the present study was to investigate the effects of hypothermia and CPB on the four variables.

METHODS

Patients

Approval of the Ethics Committee and informed consent for the study were obtained from 12 patients. The patients' demographics are shown in table 1.

Anaesthetic management

All patients were premedicated with temazepam 30 mg, ranitidine 150 mg and metoclopramide 10 mg, given orally 2 hours before induction of anaesthesia. Anaesthesia was induced and maintained with target controlled infusions of propofol [22] and alfentanil [23]. The target controlled infusion system for propofol was operated by a three compartment pharmacokinetic model "Diprifusor". The target concentrations that were set at each period during anaesthesia are shown in figure 1. Pancuronium was used to provide neuromuscular block. Monitoring during surgery included invasive arterial pressure, ECG, pulse oximetry, central venous pressure, and nasopharyngeal and oesophageal temperatures.

Management of extracorporeal circulation and hypothermia

The bypass circuit was of standard construction; we used a membrane oxygenator and arterial line filter. The circuit was primed with 1.6 litres of Ringer's lactate solution. The flow rate was set at 2.4 L min$^{-1}$ m$^{-2}$ during cooling and was increased during rewarming to maintain venous blood haemoglobin oxygen saturation above 70 %. Changes of nasopharyngeal temperature during anaesthesia are shown in figure 2.

Surface EEG Analyses

The EEG was obtained from four disposable silver-silver chloride electrodes (Zipprep, Aspect Medical Systems, MA, U.S.A.) placed on both sides of the outer malar bone (At1 and At2), Fpz as the reference and Fp1 as the ground. Impedance of the electrodes was confirmed to be less than 2000 ohm. The BIS, MF and 95% SEF were measured using an EEG monitor (A-1000, BIS 3.1 algorithm. rev. 3.12 software, Aspect Medical Systems, MA, U.S.A.). The BIS, MF and 95% SEF required at least 30 s to be fully updated. The values were stored automatically on a microcomputer (T1950CT, Toshiba, Japan) at 5 s intervals. The EEG before induction of anaesthesia was obtained with the patient's eyes closed.

Auditory evoked potentials acquisition

The AEP were obtained using a similar system to that described in our previous studies [15][20] from three electrodes (Zipprep) placed on the right mastoid (+), middle forehead (-) and Fp2 as the reference. The amplifier was custom-built with a 5 kV medical grade isolation. It had a common mode rejection ratio of 170 dB with balanced source impedance, input voltage noise of 0.3 µV (10 Hz - 1 kHz rms) and current input noise of 4 pA (0.05 Hz - 1 kHz rms). A third-order Butterworth analogue band-pass filter with a bandwidth of 1-220 Hz was used. The clicks were 70 dB above the normal hearing threshold and had a duration of 1 ms. They were presented at a rate of 6.9 Hz to both ears. The amplified EEG was sampled at 1773 Hz by a 12-bit analogue to digital converter (PCM-DAS08, Computer Boards Inc., MA. U.S.A.) and was processed in real-time by the microcomputer. AEP were produced by averaging 256 sweeps of 144 ms duration. The time required to have a full update of the signal was 36.9 s, but a moving time averaging technique allowed a faster response time to any change in the signal. AEP were obtained at 3 s intervals. The AEPIndex is a mathematical derivative reflecting morphology of the AEP. The value was calculated as the sum of the square root of the absolute difference between every two successive 0.56 ms segment of the AEP waveform [19].

Data analyses

Each variable was recorded simultaneously and averaged values for 15 seconds were obtained at 10 periods; before induction of anaesthesia, 5 minutes after induction, 5 minutes before start of CPB, during CPB (5, 10, 20 and 30 minutes elapsed, and 5 minutes before end of CPB), 5 and 30 minutes after end of CPB. The values of the four variables were analysed using the Kruskal-Wallis test with the Dunnett test. For evaluation of the effects of CPB on the four variables, the values of 5 minutes before and 5 minutes after start of CPB were analysed with Wilcoxon's single rank sum test. $p<0.05$ was considered statistically significant. The correlation between the four variables and nasopharyngeal temperature during cooling were also analysed with linear regression analysis. The values of the four variables were averaged for interval of 15 seconds and were sampled between one minute before start of CPB and the period when the nasopharyngeal temperature became minimum.

RESULTS

Anaesthesia was uneventful for all 12 patients. No patients had recall of intraoperative events. We did not observe sweating and tear formation in any patients. Anaesthesia related data are shown in table 2. Changes of arterial pressures and heart rate were shown in figures 3 and 4.

Changes of the four variables during anaesthesia

Changes of the four variables at the ten periods during anaesthesia are shown in figures 5 and 6. Following induction of anaesthesia, all four variables decreased but only the AEPIndex was significantly different between before and 5 minutes after induction of anaesthesia. The values of AEPIndex and BIS before and after CPB were completely separated from those before induction of anaesthesia without any overlapping but the values of SEF and MF were not. The values of the four variables were not different between before and after the start of CPB. During CPB, the values of AEPIndex, MF and SEF were tightly distributed. The values of SEF at 20 minutes and 30 minutes after the start of CPB, and that of AEPIndex at 30 minutes after start of CPB were smaller than those at 5 minutes before CPB. The values of BIS were very variable among the patients during CPB, especially during hypothermia and overlapped with those before induction of anaesthesia. When the value of BIS were above 80 during hypothermia, the raw EEG demonstrated burst and suppression pattern. The variability decreased during rewarming. The values of AEPIndex throughout the anaesthesia never overlapped with those before induction of anaesthesia.

Correlation between the four variables and nasopharyngeal temperature during cooling During the cooling phase of CPB, the values of AEPIndex, BIS and SEF slightly decreased with decreasing nasopharyngeal temperature (Figures 7-10). The correlation coefficient was the largest in SEF. Although AEPIndex and SEF were tightly distributed between 36 and 27 °C, the values of BIS were widely spread below 32 °C (Figure 8). The values of MF were widely spread above 31 °C, but were tightly distributed below 31 °C. Although the correlation was weak, the values of MF slightly increased with decreasing nasopharyngeal temperature.

DISCUSSION

Neurophysiological changes during hypothermia are characterised by decreased resting potential and decreased amplitude but increased duration of action potential, reduction of nerve conduction velocity, and impairment of synaptic transmission following reduced neurotransmitter release [24]. In unanaesthetised experimental animals, cooling to 33 °C may produce cerebral stimulatory effects as reflected by arousal phenomena, increased amplitude in evoked potentials, and hyper-responsive reflexes [25]. At that time, EEG spectra shift to theta-activity as well as to beta-activity. Functional suppression occurs at temperatures below 32 °C. In the clinical situation, however, the neurophysiological changes may be modified by various anaesthetic agents.

In the present study, propofol and alfentanil are the principal anaesthetic agents that should affect neurophysiological activity. Because propofol has been reported to suppress markedly the AEP [26], BIS [27], SEF [5] and MF [6] in dose dependent fashion, changes in propofol blood concentration, especially its protein unbinding fraction, should affect the results. In the present study, the mean target propofol blood concentration was managed within a narrow range. The target control infusion system normally produces small discrepancies between the calculated and actual blood concentrations with a bias (the mean prediction error) of -2 %, and precision (the mean of the individual absolute prediction errors) of 15.1 % [28]. However, hypothermic CPB increases the distribution volume of propofol [29],[30] and may lead to sequestration of propofol by the CPB circuit [31]. In addition, metabolism of propofol may be decreased, and haemodilution and heparin administration increase the protein unbound fraction of propofol [29]. Therefore there might be large discrepancy between the target and actual concentrations of propofol and it is difficult to predict the changes of free propofol concentration at the effector site during the CPB.

Although the target blood concentrations of propofol at 5 minutes after the start of CPB were almost same as those of 5 minutes before the start of CPB, the actual blood concentration of propofol might be different between the two periods. In spite of the possible change of the propofol concentrations, the values of all four variables at 5 minutes after the start of CPB were almost same as those of 5 minutes before the start CPB. This suggested that CPB does not affect the electrophysiological variables when propofol is infused with the "Diprifusor" target controlled infusion system to maintain the blood concentration to be stable.

The target alfentanil plasma concentration was set at high values before CPB and gradually decreased during and after CPB. However, this change of alfentanil plasma concentration should not affect the measurements because alfentanil has only slight effects on the electrophysiological variables [32].

Several studies [12],[13] reported that the BIS was much superior to former EEG derivatives to detect awareness and to predict movement induced by surgical stimulation during non cardiac anaesthesia. However, in the present study, the BIS was distributed very widely during hypothermia whereas the other three variables were distributed more tightly. We evaluate all the patients were unconscious throughout the anaesthesia because there was no recall of intraoperative events, no sweating and tear formation. We also believe the patients were deeply anaesthetised and were unconscious when the BIS was high during hypothermia because the raw

SUBSTITUTE SHEET (RULE 26)

EEG showed burst and suppression pattern at that occasion. This finding suggested that the algorithm used to calculated the BIS had some serious problems in processing the EEG during hypothermia especially at burst and suppression EEG.

Hett and colleagues [21] reported that the MLAEP was suppressed at 28 ¡C during CPB with decreased amplitude of Pa and Nb and increased latency of Pa and Nb. In the present study, the values of AEPIndex decreased linearly during the cooling phase of CPB. These two finding are comparable with each other. Although Hett and colleagues reported the amplitude of Pa and Nb after CPB were larger than those before CPB, the AEPIndex in the present study did not change at the start of CPB. This inconsistency may depend on the difference in anaesthetic methods used; the target control infusions of propofol and alfentanil in our study, and intermittent injection of fentanyl with nitrous oxide and isoflurane, substituted by propofol infusion during CPB, in Hett's study. The present study demonstrated that AEPIndex markedly decreased after induction of anaesthesia and the values were distributed tightly mainly below 40 throughout anaesthesia. This finding suggests that the AEPIndex could provide reliable information to distinguish consciousness from unconsciousness. The AEPIndex of below 40 could be considered as reflecting adequate anaesthesia regardless of body temperature.

In previous studies, the relationships between SEF and body temperature were not consistent. Russ and colleagues [7] reported that the SEF was correlated linearly with nasopharyngeal temperature during cooling with fentanyl and nitrous oxide anaesthesia. On the contrary, Levy and colleagues [8] did not find any temperature dependent changes of SEF during rewarming with fentanyl, halothane or isoflurane anaesthesia. Bashein and colleagues [9] could not find any general definition of the normal EEG response to hypothermia with fentanyl, diazepam and enflurane anaesthesia, because of large interpatient variability. In the present study, SEF correlated well with nasopharyngeal temperature. The inconsistency among the four studies may depend on differences between the anaesthetic methods used. Although both SEF and MF were distributed tightly during hypothermia, their values before induction were spread widely and were not discriminated clearly from those during anaesthesia. This finding suggested that SEF and MF did not have adequate characteristics as a desirable depth of anaesthesia monitor during cardiac anaesthesia.

In conclusions, all four variables were not affected by the transition to CPB. During hypothermia AEPIndex, MF and SEF were tightly distributed but BIS was not. The AEPIndex was the most stable and reliable as a depth of anaesthesia monitor among the four variables in cardiac bypass surgery.

REFERENCES

[1] Kochs E. Electrophysiological monitoring and mild hypothermia. *Journal of Neurosurgical Anaesthesiology* 1995; 7: 222-228.

[2] Schwender D, Daunderer M, Mulzer S, Klasing S, Finsterer U, Peter K. Spectral edge frequency of the electroencephalogram to monitor "depth" of anaesthesia with isoflurane or propofol. *British Journal of Anaesthesia* 1996; 77: 179-184.

[3] Leslie K, Sessler DI, Smith WD, Larson MD, Ozaki M, Blanchard D, Crankshaw DP. Prediction of movement during propofol/nitrous oxide anesthesia. *Anesthesiology* 1996; 84: 52-63.

[4] Gaitini L, Vaida S, Collins G, Somri M, Sabo E. Awareness detection during caesarean section under general anaesthesia using EEG spectrum analysis. *Canadian Journal of Anaesthesia* 1995; 42: 377-381.

[5] Traast HS, Kalkman CJ. Electroencephalographic characteristics of emergence from propofol /sufentanil total intravenous anesthesia. *Anesthesia and Analgesia* 1995; 81: 366-371.

[6] Schwilden H, Stoeckel H, Schüttler J. Closed-loop feedback control of propofol anaesthesia by quantitative EEG analysis in humans. *British Journal of Anaesthesia* 1989; 62: 290-296.

[7] Russ W, Kling D, Sauerwein G, Hempelmann G. Spectral analysis of the EEG during hypothermic cardiopulmonary bypass. *Acta Anaesthesiologica Scandinavica* 1987; 31: 111-116.

[8] Levy WJ. Quantative analysis of EEG changes during hypothermia. *Anesthesiology* 1984; 60: 291-297.

[9] Bashein G, Nessly ML, Bledsoe SW, Townes BD, Davis KB, Coppel DB, Hornbein TF. Electroencephalography during surgery with cardiopulmonary bypass and hypothermia. *Anesthesiology* 1992; 76: 878-891.

[10] Flaishon R, Sebel PS, Sigl J. Detection of consciousness following thiopental: isolated forearm and bispectral EEG (BIS). *Anesthesiology* 1995; 83: A515

[11] Kearse L, Rosow C, Sebel P, Bloom M, Glass P, Howell S, Greenwald S. The Bispectral Index correlates with sedation/hypnoses and recall: comparison using multiple agents. *Anesthesiology* 1995; 83: A507

[12] Kearse LA, Jr., Manberg P, Chamoun N, DeBros F, Zaslavsky. Bispectral analysis of the electroencephalogram correlates with patient movement to skin incision during propofol/nitrous oxide anesthesia. *Anesthesiology* 1994; 81: 1365-1370.

[13] Vernon JM, Lang E, Sebel PS, Manberg P. Prediction of movement using bispectral electroencephalographic analysis during propofol/alfentanil or isoflurane/alfentanil anesthesia. *Anesthesia & Analgesia* 1995; 80: 780-785.

[14] Thornton C, Konieczko KM, Knight AB, et al. Effect of propofol on the auditory evoked response and oesophageal contractility. *British Journal of Anaesthesia* 1989; 63: 411-417.

[15] Davies FW, Mantzaridis H, Fisher AC, Kenny GN, Fisher C. Middle latency auditory evoked potentials during repeated transitions from consciousness to unconsciousness. *Anaesthesia* 1996; 51: 107-113.

[16] Newton DE, Thornton C, Konieczko KM, et al. Auditory evoked response and awareness: a study in volunteers at sub- MAC concentrations of isoflurane. *British Journal of Anaesthesia* 1992; 69: 122-129.

[17] Kenny GN, Davies FW, Mantzaridis H, Fisher AC. Transition between consciousness and unconsciousness during anesthesia. *Anesthesiology* 1993; 79: A330.

[18] Kenny GN, McFadzean WA, Mantzaridis H, Fisher AC. Closed-loop control of anesthesia. *Anesthesiology* 1992; 77: A328

[19] Mantzaridis H. Development of an AEP system, In: Ph D thesis: Closed loop control of anaesthesia. Strathclyde University, Glasgow, 1996;in press.

[20] Doi M, Gajraj RJ, Mantzaridis H, Kenny GNC. Relationship between calculated blood concentration of propofol and electrophysiological variables during emergence from anaesthesia: a comparison of Bispectral Index, spectral edge frequency, median frequency and Auditory Evoked Potential Index *British Journal of Anaesthesia*.

[21] Hett DA, Smith DC, Pilkington SN, Abbott TR. Effect of temperature and cardiopulmonary bypass on the auditory evoked response *British Journal of Anaesthesia* 1995; 75:293-296.

[22] Kenny GN, White M. A portable target controlled propofol infusion system. *International Journal of Clinical Monitoring and Computing* 1992; 9: 179-182.

[23] Davies FW, White M, Kenny GNC. Postoperative analgesia using a computerised infusion of alfentanil following aortic bifurcation graft surgery. *International Journal of Clinical Monitoring and Computing* 1992; 9: 207-212.

[24] Markand ON, Warren CH, Moorthy SS. Monitoring of multimodality evoked potentials during open heart surgery under hypothermia. *Electroencephalography and Clinical Neurophysiology* 1984; 59: 432-440.

[25] Blair E. A physiological classification of clinical hypothermia. *Surgery* 1965; 58: 607-618.

[26] Chassard D, Joubaud A, Colson A, et al. Auditory evoked potentials during propofol anaesthesia in man. *British Journal of Anaesthesia* 1989; 62: 522-526.

[27] Leslie K, Sessler DI, Schroeder M, Walters K. Propofol blood concentration and the Bispectral Index predict suppression of learning during propofol/epidural anesthesia in volunteers. *Anesthesia & Analgesia* 1995; 81: 1269-1274.

[28] Davidson JA, Macleod AD, Howie JC, White M, Kenny GN. Effective concentration 50 for propofol with and without 67 % nitrous oxide. *Acta Anaesthesiologica Scandinavica* 1993; 37: 458-464.

[29] Russell GN, Wright EL, Fox MA, Douglas EJ, Cockshott ID. Propofol-fentanyl anaesthesia for coronary artery surgery and cardiopulmonary bypass. *Anaesthesia* 1989; 44: 205-208.

[30] Massey NJA, Sherry KM, Oldroyd S, Peacock JE. Pharmacokinetics of an infusion of propofol during cardiac surgery. *British Journal of Anaesthesia* 1990; 65: 475-479.

[31] Hynyen M, Mammaren E, Rosenberg P. Propofol sequestration within the extracorporeal circuit. *Canadian Journal of Anaesthesia* 1994; 41: 583-588.

[32] Schwender D, Rimkus T, Heassler R, Klasing S, Pöppel E, Peter K. Effects of increasing doses of alfentanil, fentanyl and morphine on mid-latency auditory evoked potentials. *British Journal of Anaesthesia* 1993; 71: 622-628.

Legends

Figure 1

Changes of the target blood concentrations (mean ± SD, n = 12) of propofol (O) and alfentanil (■) at nine periods during anaesthesia; 5 minutes after induction, 5 minutes before start of CPB, during CPB (5, 10, 20 and 30 minutes elapsed, and 5 minutes before end of CPB), 5 and 30 minutes after end of CPB.

Figure 2

Changes of nasopharyngeal temperature (mean ± SD, n = 12) at nine periods during anaesthesia: 5 minutes after induction, 5 minutes before start of CPB, during CPB (5, 10, 20 and 30 minutes elapsed. and 5 minutes before end of CPB), 5 and 30 minutes after end of CPB.

Figure 3

Changes of systolic (▼) and diastolic (▲) arterial pressures during anaesthesia. mean ± SD, n = 12; before induction of anaesthesia, 5 minutes after induction, 5 minutes before start of CPB. during CPB (5, 10, 20 and 30 minutes elapsed, and 5 minutes before end of CPB), 5 and 30 minutes after end of CPB.

Figure 4

Changes of heart rate (mean ± SD, n = 12) at ten periods during anaesthesia; before induction of anaesthesia, 5 minutes after induction, 5 minutes before start of CPB.

during CPB (5, 10, 20 and 30 minutes elapsed, and 5 minutes before end of CPB), 5 and 30 minutes after end of CPB.

Figure 5 Changes of AEPIndex (●) and BIS (□) at ten periods during anaesthesia; before induction of anaesthesia, 5 minutes after induction, 5 minutes before start of CPB, during CPB (5, 10, 20 and 30 minutes elapsed, and 5 minutes before end of CPB), 5 and 30 minutes after end of CPB. Data are mean ± range, n = 12. *: $p<0.05$ compared with the value before induction of anaesthesia. #: $p<0.05$ compared with the value 5 minutes before the start of CPB.

Figure 6

Changes of SEF (Δ) and MF (◆) at ten periods during anaesthesia; before induction of anaesthesia, 5 minutes after induction, 5 minutes before start of CPB, during CPB (5, 10, 20 and 30 minutes elapsed, and 5 minutes before end of CPB), 5 and 30 minutes after end of CPB. Data are mean ± range, n = 12. *: $p<0.05$ comparing with the value before induction of anaesthesia. #: $p<0.05$ comparing with the value 5 minutes before start of CPB.

Figure 7

The correlation between nasopharyngeal temperature and AEPIndex during cooling.
AEPIndex = 0.713 Nasopharyngeal temperature − 4.488, r = 0.409

Figure 8

The correlation between nasopharyngeal temperature and BIS during cooling.

BIS = 1.883 Nasopharyngeal temperature - 18.463, r = 0.0334

Figure 9

The correlation between nasopharyngeal temperature and SEF during cooling. SEF = 0.564 Nasopharyngeal temperature - 5.731, r = 0.683

Figure 10

The correlation between nasopharyngeal temperature and MF during cooling.

MF = -0.089 Nasopharyngeal temperature + 6.859, r = 0.246

APPENDIX 2

Analysis of the EEG bispectrum, auditory evoked potentials and the EEG power spectrum during repeated transitions from consciousness to unconsciousness

R. J. GAJRAJ, M. DOI, H. MANTZARIDIS AND G. N. C. KENNY

R. J. GAJRAJ, DM, FRCA, Research Fellow;

G. N. C. KENNY, BSC (HONS), MD, FRCA, Professor and Head;

University Department of Anaesthesia, HCI International Medical Centre, Beardmore Street, Clydebank, G81 4HX, Scotland.

M. DOI, MD, Assistant Professor,

Department of Anesthesiology and Intensive Care, Hamamatsu University School, of Medicine, 3600 Handa, Hamamatsu 431-31, Japan.

H. MANTZARIDIS, MB CHB, PHD, Senior House Officer,

Department of Anaesthetics, Law Hospital, Carluke, Lanarkshire ML8 5ER, Scotland.

Correspondence to Professor G.N.C. Kenny.

Running title: EEG analysis during conscious and unconscious states.

Summary

We compared the auditory evoked potential (AEP) Index (a numerical index derived from the AEP), the 95% spectral edge frequency (SEF) and median frequency (MF) and the bispectral index (BIS) during alternating periods of consciousness and unconsciousness produced by target controlled infusions of propofol. Twelve patients undergoing hip or knee replacement under spinal anaesthesia were studied. During periods of consciousness and unconsciousness, respective mean (SD) values for the four measurements were: AEP Index of 60.8 (13.7) and 37.6 (6.5); BIS of 85.1 (8.2) and 66.8 (10.5); SEF of 24.2 (2.2) and 18.7 (2.1), and MF of 10.9 (3.3) and 8.8 (2.0). Threshold values with a specificity of 100% for a state of unconsciousness were: an AEP Index of 37 (sensitivity 52%), a BIS of 55 (sensitivity 15%) and a SEF of 16.0 (sensitivity 9%). There was no recorded value of the MF that was 100% specific for unconsciousness. Of the four measurements, only the AEP Index demonstrated a significant difference ($P < 0.05$) between all mean values one minute before recovery of consciousness and all mean values one minute after recovery of consciousness. Our findings suggest that of the four electrophysiologic variables, the AEP Index is best at distinguishing the transition from unconsciousness to consciousness.

Key words: auditory evoked potential index, auditory evoked potentials, bispectral index, spectral edge frequency, median frequency, depth of anaesthesia, consciousness.

The ability to detect recovery of consciousness from a state of unconsciousness is an essential attribute of a monitor of anaesthetic depth, so that awareness under anaesthesia may be prevented. While an ideal method of assessment of anaesthetic depth remains an elusive goal, it has been suggested that monitoring of auditory evoked potentials (AEP)[1-3] or bispectral electroencephalographic (EEG) analysis[4-8] may be more reliable than other techniques. Recently the AEP Index (formerly known as the Level of Arousal Score), a mathematical derivative which reflects AEP waveform morphology that is calculated from the amplitude difference between successive segments of the AEP curve,[9] has been investigated as a means of assessment of anaesthetic depth.[10-12] The median frequency (MF)[13,14] and the 95% spectral edge frequency (SEF)[7,15] of the EEG power spectrum have also been investigated for assessing anaesthetic depth and have been incorporated into commercially available monitors for this purpose.

In a recent study, our group observed that while the BIS and to a lesser extent the SEF correlated well with predicted blood propofol concentrations during recovery from anaesthesia, the AEP Index was best at distinguishing consciousness from unconsciousness.[16] The present study was therefore designed to investigate further the ability of the AEP Index, the BIS, the SEF and the MF to identify awareness by their capacity to detect recovery of consciousness. We assessed changes in these electrophysiological measurements during alternating periods of unconsciousness and consciousness, investigated the reproducibility of these changes in each patient and analysed the amount of inter-patient variability.

Patients and Methods

After obtaining Hospital Ethics Committee approval and informed consent, 12 patients scheduled for orthopaedic surgery (hip or knee replacement) under spinal anaesthesia were included in the study. Two (2) male patients and 10 female patients with a mean (range) age of 73.8 (62-82) yr and a mean (range) weight of 70.7 (55-84) kg completed the study. Patients with psychiatric or hearing abnormalities were excluded from the study.

All patients were premedicated with temazepam 30 mg given 2 hours before surgery. Spinal anaesthesia was established with either 3.0 - 3.5 ml of 0.5% or 3 ml of 0.75% plain bupivacaine administered via a 26 G needle at the L 2-3 interspace. An epidural catheter was also inserted for administration of top-ups during surgery in prolonged cases.

After ensuring adequate regional anaesthesia for surgery, a target controlled infusion (TCI)[17] of propofol was commenced and oxygen administered via a nasal sponge. One anaesthetist was responsible for standard monitoring of the patient and for manipulating the TCI propofol to produce alternating periods of consciousness and unconsciousness. Two investigators were present in addition to the anaesthetist responsible for conducting the anaesthetic. One investigator observed the AEP system and the EEG monitor, and recorded the timing of events such as the onset of unconsciousness and consciousness. At intervals of 30 s, the second investigator established the presence or absence of an eyelash reflex and the patient's response to a verbal command to squeeze the investigator's hand. The transition from consciousness to unconsciousness was defined as the point at which loss of response to the verbal command occurred, and the return of this response was considered the transition from unconsciousness to consciousness.

AUDITORY EVOKED POTENTIAL MONITORING

Auditory evoked potentials were monitored as described in our previous studies.[16,18] The EEG was obtained from three disposable silver-silver chloride electrodes (Zipprep, Aspect Medical Systems. USA) placed on the right mastoid (+), middle forehead (-) and $Fp_2$ as the reference. The custom-built amplifier had a 5 kV medical grade isolation, common mode rejection ratio of 170 dB with balanced source impedance, input voltage noise of 0.3 μV and current input noise of 4 pA (0.05 Hz - 1 kHz rms). A third-order Butterworth analogue band-pass filter with a bandwidth of 1-220 Hz was used. The auditory clicks were of 1 ms duration and 70 dB above the normal hearing threshold. They were presented to the right ear at a rate of 6.9 Hz. The amplified EEG was sampled at a frequency of 1778 Hz by a high accuracy, low distortion 12-bit analogue to digital converter (PCM-DAS08, Computer Boards Inc., USA) and processed in real-time by a microcomputer (T1950CT, Toshiba, Japan).

The AEP were produced by averaging 256 sweeps of 144 ms duration. The time required to have a full update of the signal was 36.9 s, but a moving time averaging technique allowed a faster response time to any change in the signal. Averaged curves were obtained at 3 s intervals.

The AEP Index, which reflects the morphology of the AEP curves, allowed on-line analysis of the AEP. It is calculated as the sum of the square root of the absolute difference between every two successive 0.56 ms segments of the AEP waveform.' The AEP and other data were stored automatically on the microcomputer's hard disk every 3 seconds, enabling future retrieval for further analysis.

EEG BISPECTRAL AND POWER SPECTRAL ANALYSIS

The EEG was obtained from four Zipprep electrodes placed on both sides of the outer malar bone ($At_1$ and $At_2$) with Fpz as the reference and $Fp_1$ as the ground. The EEG bispectrum, SEF and MF were monitored using a commercially available EEG monitor (A-1000, BIS 3.0 algorithm, rev. 0.40 software, Aspect Medical Systems, USA). The update rate on the Bispectral index monitor was set to 10 seconds with the bispectral smoothing function switched off. Data from the A-1000 EEG monitor were downloaded automatically and stored on the microcomputer every 5 seconds.

Both monitoring systems (AEP and EEG) had sophisticated artefact rejection algorithms and the amplifiers of both also had medical grade isolation. Furthermore, the auditory clicks that produced the AEP generate signals 100 times smaller than the remainder of the EEG. Therefore, although the AEP and EEG were monitored simultaneously, there would have been no intereference between the two systems that could have affected the results.

DATA ANALYSIS

Periods of consciousness and unconsciousness extended between the time of recovery of consciousness (response to verbal command) and the time when consciousness was lost (loss of response to verbal command). However, the periods from one minute before until one minute after transitions from one state of consciousness to the next were excluded when conscious and unconscious values of each measurement were analysed. These periods were excluded because they were likely to contain values representative of both consciousness and unconsciousness, since 36.9 seconds were required to obtain a full update of the AEP Index (and 30 s for the BIS), and patients were also most likely to be drifting in and out of consciousness during these periods. Therefore, conscious values were considered to be those recorded during periods from 1 minute after regaining consciousness until 1 minute before the next loss of consciousness (fig. 1). Unconscious values were those recorded during periods from 1 minute after loss of consciousness until 1 minute before the next recovery of consciousness (fig. 1).

To investigate the ability of the electrophysiologic variables to detect awareness, values recorded 1 minute before recovery of consciousness were compared with values at 1 minute after consciousness returned (fig. 1). All patients had at least three transitions from unconsciousness to consciousness. Therefore, the first three transitions were used to compare the ability of the different measurement systems to detect these transitions.

The mean, standard deviation (SD) and range of values of each measurement occurring during all periods of consciousness and unconsciousness, were determined by analysing all conscious and unconscious values respectively, recorded over the course of the entire study. These measurements made during all periods of unconsciousness and consciousness were used to determine threshold values with 100% specificity and threshold values with approximately 85% sensitivity. Statistical analysis was with Minitab 10.5 for Windows, using ANOVA with Tukey's test. $P < 0.05$ was considered significant.

All patients were interviewed on the day after surgery about their memory of intraoperative events. They were also questioned about their satisfaction with the auditory clicks and the technique of monitoring.

Results

The mean (range) duration of surgery was 74 (58-121) minutes. There was a mean (range) of 10 (6 - 20) periods of consciousness and unconsciousness.

Auditory Evoked Potential Index

Table 1 shows the mean (range) of AEP Index, BIS, SEF and MF values recorded during all conscious or unconscious periods as defined above. Table 2 shows threshold values of the four measurements with 100% specificity and threshold values with close to 85% sensitivity for states of consciousness and unconsciousness. In total, 4,823 unconscious and 2,055 conscious values of the AEP Index, and 2,885 unconscious and 1,322 conscious values of the BIS, SEF and MF were analysed. A threshold value of the AEP Index of 37 had a specificity of 100% and a sensitivity of 52% for a state of unconsciousness. A threshold value of 56 was 60% sensitive and 100% specific for consciousness. Figure 2 shows the mean (SD) AEP Index and BIS before and after the first 3 transitions from unconsciousness to consciousness. All mean awake values 1 minute after return of consciousness were significantly higher than all mean unconscious values 1 minute before ($P < 0.05$). AEP Index values during periods of consciousness were more variable than values during unconsciousness (fig. 2, table 1).

Bispectral Index

Table 1 shows that, unlike the AEP Index, some BIS values during unconsciousness were higher than the *mean* value during consciousness, and some conscious values were also lower than the *mean* value during unconsciousness. A BIS of 55 had a specificity of 100% but was only 15% sensitive for a state of unconsciousness (table 2). A very high value of 95 was required for 100% specificity for consciousness and was only 14% sensitive. Figure 2 shows the mean (SD) BIS at 1 minute before and after the first 3 transitions from unconsciousness to consciousness. Unlike the AEP Index, mean awake values 1 minute after return of consciousness were not *all* significantly different from mean unconscious values 1 minute before regaining consciousness ($P < 0.05$). The BIS also contrasted with the AEP Index in that values recorded during unconsciousness demonstrated more inter-patient variability than values during periods of consciousness (table 1).

Spectral Edge Frequency

Comparable to the BIS but unlike the AEP Index, some SEF values during unconsciousness were higher than the *mean* value during consciousness, and some conscious values were lower than the *mean* value during unconsciousness (table 1). A SEF of 16.0 Hz had a specificity of 100% but only 9% sensitivity for a state of unconsciousness (table 2). A value of 26.6 Hz was 100% specific but only 15% sensitive for consciousness. Figure 3 shows the mean (SD) SEF and MF at 1 minute before and after the first 3 transitions from unconsciousness to consciousness. Like the BIS but unlike the AEP Index, mean awake values of the SEF 1 minute after the return of consciousness were not *all* significantly different from mean unconscious values 1 minute before regaining consciousness ($P < 0.05$). Similar to the AEP Index but unlike the BIS, awake values of the SEF were generally more variable than values recorded during periods of unconsciousness (fig. 3).

Median Frequency

Similar to the BIS and the SEF, some values of the MF during unconsciousness were higher than the *mean* value during consciousness, and some conscious values were lower than the *mean* value during unconsciousness (table 1). The lowest recorded awake value of the MF was lower than the minimum MF value during unconsciousness (table 1) so that a value of 1.4 Hz, which was never attained, would have been 100% specific for unconsciousness (table 2). A MF value of 13.8 Hz was 100% specific but only 18% sensitive for consciousness. Figure 3 shows the mean (SD) MF at 1 minute before and after the first 3 transitions from unconsciousness to consciousness. Although mean awake values of the MF tended to be numerically

SUBSTITUTE SHEET (RULE 26)

greater than mean values during unconsciousness, all mean conscious and unconscious values were not significantly different. There was relatively large interpatient variability of MF values during both consciousness and unconsciousness, and like the AEP Index and the SEF but unlike the BIS, this variability was greater during periods of consciousness (fig. 3).

No patient had recall of any event in theatre, including the application of the earphones and the auditory clicks. All patients were satisfied with the anaesthetic technique and were happy to have the same technique of monitoring for any future anaesthetic.

Discussion

Although consistent changes (increased latency and decreased amplitude) in middle latency auditory evoked potential (AEP) waves occur as anaesthesia is deepened, it is difficult to analyse AEP waves in real time and to quantify changes in the clinical situation. The AEP Index, a mathematical derivative that reflects AEP waveform morphology,[9] allows on line assessment of the AEP during anaesthesia and surgery. Conventional EEG processing techniques such as those used to measure the spectral edge frequency (SEF) and the median frequency (MF) ignore the interfrequency phase information in the EEG and may be unreliable for monitoring the level of anaesthesia due to the variable effects produced by different anaesthetic agents and the large interpatient variability.[19] Unlike power spectrum analysis, bispectral EEG analysis

SUBSTITUTE SHEET (RULE 26)

also quantifies the phase coupling between component EEG frequencies.[20] The Bispectral Index (BIS), a numerical value derived from the EEG bispectrum, has been shown to possess characteristics desirable in an anaesthetic depth monitor, such as the capacity to predict movement in response to surgery[1,21] and to detect consciousness[22-24] when using a variety of anaesthetic drugs.

The ability to distinguish consciousness from unconsciousness is an essential feature of a monitor of depth of anaesthesia, and was the clinical end point used in this study, circumventing the problem of the absence of a universally accepted standard by which to compare such monitors under investigation.

The assumption that awareness, and therefore consciousness, is indicated by a response to command has been made in previous studies.[25,26] However, intraoperative awareness may occur without postoperative recall,[27] as occurred in all of our patients. Nevertheless, the prevention of the dreaded consequence of intraoperative awareness without amnesia, especially in the presence of inadequate analgesia, is one of the most important functions of anaesthetic depth monitors. Amnesia for intraoperative events may have occurred in our patients because of the use of benzodiazepine premedication[28] or from general anaesthetic drugs.[29,30]

The present study demonstrated the potential of the AEP Index to detect recovery of consciousness. Of the four electrophysiologic variables studied, only the AEP Index demonstrated a significant difference ($P < 0.05$) between all mean values one minute before recovery of consciousness and all mean values one minute after recovery of consciousness (fig. 2). The clear distinction between conscious and unconscious values of the AEP Index was also demonstrated by the fact that it was the only measurement in the present study whose lowest recorded conscious value was higher than the mean unconscious value, and whose highest unconscious value was lower than the mean conscious score.

Although other studies[22-24] have shown the BIS to be capable of detecting consciousness, in the present study the BIS was unable to achieve statistical significance when points 1 minute before and after recovery of consciousness were compared. This could be explained by the gradual increase in the BIS which frequently occurs during emergence from anaesthesia.[31,32] Values recorded 2 minutes apart (1 minute before and after recovery) would therefore be more similar to each other than corresponding AEP Index values, which increase suddenly at the time of awakening.[16] Figure 4, which is a graph of changes in AEP Index and BIS for one of the patients in the present study, demonstrates this gradual increase in BIS during the first transition from unconsciousness to consciousness. In contrast, the AEP Index increased sharply at all three transitions in this patient.

The MF was least capable of distinguishing consciousness from unconsciousness, as all mean conscious and unconscious values were similar to each other (fig. 3). Studies by Schwilden and colleagues have suggested that MF values below approximately 5 Hz indicate unconsciousness and that values of 2-3 Hz indicate a satisfactory depth of anaesthesia.[13,33-35] The difference between our findings and those of Schwilden and co-workers may be explained by differences in methodology and by the effects of EEG burst suppression which lead to misinterpretation of the EEG power spectrum.[36] In addition, there is possibly a lag between changes in MF and changes in anaesthetic concentration during recovery which could explain the *lower* values during conscious periods and *higher* unconscious values demonstrated in one of the patients in the present study (fig. 5).

The already low frequency of awareness under anaesthesia of 0.1%,[2,37] and the potentially disastrous consequences of its occurrence, suggest that we should be attempting to develop monitors that will almost guarantee its elimination by reliably detecting unconsciousness. Such a monitor should be capable of providing information that is specific for unconsciousness at a level of anaesthesia that is not excessive. A BIS value of 55 was 100% specific but only 15% sensitive for unconsciousness (table 2). Additionally, a threshold value of 95 was necessary for 100% specificity for consciousness, as there were very high values of the BIS recorded during periods of unconsciousness. These findings suggest that the BIS could not be used to direct anaesthetic administration to *ensure* unconsciousness without the risk of excessive anaesthesia. Values of the BIS which are specific for unconsciousness are not sensitive enough, and some adequately anaesthetised (clinically unconscious) patients have BIS values of fully awake subjects.

A similar problem of excessive anaesthesia may occur if the SEF is used to ensure unconsciousness, as a value of 16.0 Hz was 100% specific but only 9% sensitive for unconsciousness. Very high SEF values were also recorded during unconsciousness so that a value of 26.6 Hz was necessary for 100% specificity for consciousness.

SUBSTITUTE SHEET (RULE 26)

In contrast, an AEP Index of 37 was 100% specific for unconsciousness, with a much greater level of sensitivity (52%) than corresponding SEF and BIS values. There was also no problem of unconscious patients with a very high AEP Index, and a value of 56 was 100% specific and 60% sensitive for consciousness. These findings suggest that it may be possible to aim for an AEP Index value that ensures unconsciousness while avoiding excessive anaesthesia.

The range of BIS values during periods of consciousness in the present study varied between 68 - 98. Other studies have reported variable BIS values of around 50 - 85 at the time of recovery of consciousness.[5,16,22-24] Flaishon and colleagues[25] reported that no unconsciousness was observed when the BIS was greater than 70 and no consciousness occurred below 65. In contrast, no consciousness was observed in the present study below a score of 55, while 36% of BIS values during unconsciousness (1,048 out of 2,885 values) were above 70. The wide variation in BIS values among these studies may be due to the use of different anaesthetic agents and to the different clinical end-points used to define consciousness.

Other studies have reported differing results for SEF and MF during consciousness and unconsciousness. The median SEF was 20.4 Hz on recovery and 10.1 Hz during anaesthesia in one of the studies in Schwilden's series[35] compared to corresponding mean values of 24.2 Hz and 18.7 Hz in the present study. However, there was large variability in SEF values in both studies. Arndt and colleagues reported that adequate anaesthesia could be expected when the SEF ranged between 14-16 Hz.[38] While a SEF of 16 Hz was 100% specific for unconsciousness in the present study (table 2), it was only 9% sensitive. Schwilden and colleagues also reported that no response to verbal command occurred below a MF of 5 Hz for a variety of drugs.[33-35] In contrast, consciousness was present in the range 2 - 19 Hz in the present study and, while 5 Hz was 94% specific for unconsciousness, it was only 7% sensitive.

The present study demonstrated the potential of the AEP Index to detect recovery of consciousness from propofol anaesthesia. Unconsciousness due to different anaesthetic agents may produce dissimilar effects on the EEG[19,39,40] and on the BIS,[21,41-44] although consistent changes have been demonstrated in MLAEP waves.[2,5,45-47] Further studies are therefore necessary to investigate the ability of these measurements to detect recovery of consciousness from anaesthesia produced by different drugs. Another limitation of the present study was the lack of influence of surgical stimuli, effectively abolished by spinal anaesthesia, on the four measurements. Surgical stimulation is known to affect the EEG[48] and the AEP.[48-50] However it would be morally and ethically challenging to design a study in which consciousness was repeatedly induced in the presence of a painful surgical wound.

Acknowledgements

We thank Dr. N. B. Scott and Dr. P. Ramayya for their assistance and permission to study patients under their care and Aspect Medical Systems for the loan of the A-1000 EEG monitor used in this study.

References

1. Jessop J, Jones JG. Evaluation of the actions of general anaesthetics in the human brain. [Review]. *General Pharmacology* 1992;23:927-935.

2. Jones JG. Perception and memory during general anaesthesia. [Review]. *British Journal of Anaesthesia* 1994;73:31-37.

3. Sharpe RM, Nathwani D, Pal SK, Brunner MD, Thornton C, Dore CJ, Newton DEF. Auditory evoked response, median frequency and 95% spectral edge during anaesthesia with desflurane and nitrous oxide. *British Journal of Anaesthesia* 1997;78:282-285.

4. Kearse LA, Jr., Manberg P, Chamoun N, DeBros F, Zaslavsky A. Bispectral analysis of the electroencephalogram correlates with patient movement to skin incision during propofol/nitrous oxide anesthesia. *Anesthesiology* 1994;81:1365-1370.

5. Kearse LA, Jr., Manberg P, DeBros F, Chamoun N, Sinai V. Bispectral analysis of the electroencephalogram during induction of anesthesia may predict hemodynamic responses to laryngoscopy and intubation. *Electroencephalography & Clinical Neurophysiology* 1994;90:194-200.

SUBSTITUTE SHEET (RULE 26)

6. Sebel PS, Bowles SM, Saini V, Chamoun N. EEG bispectrum predicts movement during thiopental/isoflurane anesthesia. *Journal of Clinical Monitoring* 1995;11:83-91.

7. Leslie K, Sessler DI, Schroeder M, Walters K. Propofol blood concentration and the Bispectral Index predict suppression of learning during propofol/epidural anesthesia in volunteers. *Anesthesia & Analgesia* 1995;81:1269-1274.

8. Liu J, Singh H, White PF. Electroencephalogram bispectral analysis predicts the depth of midazolam-induced sedation. *Anesthesiology* 1996;84:64-69.

9. Mantzaridis H, Kenny GNC. Auditory evoked potential index. A quantitative measure of changes in auditory evoked potentials during general anaesthesia. *Anaesthesia* 1997;In press:

10. Kenny GN, McFadzean W, Mantzaridis H, Fisher AC. Closed-loop control of anesthesia. *Anesthesiology* 1992;77:A328

11. Kenny GN, Davies FW, Mantzaridis H, Fisher AC. Transition between consciousness and unconsciousness during anesthesia. *Anesthesiology* 1993;79:A330

12. Kenny GN, Mantzaridis H, Fisher AC. Validation of anesthetic depth by closed-loop control. In: *Memory and Awareness in Anesthesia*. Sebel P, Bonke B, Winograd E. eds. Prentice Hall, Englewood Cliffs, 1993;225-264.

13. Schwilden H, Stoeckel H, Schuttler J. Closed-loop feedback control of propofol anaesthesia by quantitative EEG analysis in humans. *British Journal of Anaesthesia* 1989;62:290-296.

14. Traast HS, Kalkman CJ. Electroencephalographic characteristics of emergence from propofol/sufentanil total intravenous anesthesia. *Anesthesia & Analgesia* 1995;81:366-371.

SUBSTITUTE SHEET (RULE 26)

15. Gaitini L, Vaida S, Collins G, Somri M, Sabo E. Awareness detection during caesarean section under general anaesthesia using EEG spectrum analysis. *Canadian Journal of Anaesthesia* 1995;42:377-381.

16. Doi M, Gajraj RJ, Mantzaridis H, Kenny GNC. Relationship between calculated blood concentration of propofol and electrophysiological variables during emergence from anaesthesia: a comparison of bispectral index, spectral edge frequency, median frequency and auditory evoked potential index. *British Journal of Anaesthesia* 1997;78:180-184.

17. Kenny GN, White M. A portable target controlled propofol infusion system. *International Journal of Clinical Monitoring and Computing* 1992;9:179-182.

18. Davies FW, Mantzaridis H, Kenny GNC, Fisher AC. Middle latency auditory evoked potentials during repeated transitions from consciousness to unconsciousness. *Anaesthesia* 1996;51:107-113.

19. Levy WJ, Shapiro HM, Maruchak G, Meathe E. Automated EEG processing for intraoperative monitoring: a comparison of techniques. *Anesthesiology* 1980;53:223-236.

20. Sigl JC, Chamoun NG. An introduction to bispectral analysis for the electroencephalogram. *Journal of Clinical Monitoring* 1994;10:392-404.

21. Vernon JM, Lang E, Sebel PS, Manberg P. Prediction of movement using bispectral electroencephalographic analysis during propofol/alfentanil or isoflurane/alfentanil anesthesia. *Anesthesia & Analgesia* 1995;80:780-785.

22. Howell S, Gan TJ, Martel D, Glass PSA. Defining the $CP_{50}$ and $BIS_{50}$ for propofol alone and propofol with alfentanil. *Anesthesiology* 1995;83:A367

23. Flaishon R, Sebel PS, Sigl J. Detection of consciousness following thiopental: isolated forearm and bispectral EEG (BIS). *Anesthesiology* 1995;83:A515

24. Kearse L, Rosow C, Sebel P, Bloom M, Glass P, Howell S, Greenwald S. The Bispectral Index correlates with sedation/hypnosis and recall: comparison using multiple agents. *Anesthesiology* 1995;83:A507

25. Thornton C, Konieczko KM, Knight AB, Kaul B, Jones JG, Dore CJ, White DC. Effect of propofol on the auditory evoked response and oesophageal contractility. *British Journal of Anaesthesia* 1989;63:411-417.

26. Newton DE, Thornton C, Konieczko KM, Jordan C, Webster NR, Luff NP, Frith CD, Dore CJ. Auditory evoked response and awareness: a study in volunteers at sub-MAC concentrations of isoflurane. *British Journal of Anaesthesia* 1992;69:122-129.

27. Russell IF. Midazolam-alfentanil: an anaesthetic? An investigation using the isolated forearm technique. *British Journal of Anaesthesia* 1993;70:42-46.

28. Lambrechts W, Parkhouse J. Postoperative amnesia. *British Journal of Anaesthesia* 1961;33:397-404.

29. Artusio JF, Jr. Ether analgesia during major surgery. *Journal of the American Medical Association* 1955;157:33-36.

30. Rupreht J. Awareness with amnesia during total intravenous anaesthesia with propofol (letter). *Anaesthesia* 1989;44:1005

31. Sawtelle K, Rampil I. Bispectral EEG index predicts awakening. *Anesthesiology* 1994;81:A213

32. Gajraj RJ, Doi M, Kenny GNC. A comparison of auditory evoked potentials and bispectral EEG analysis in spontaneously breathing anesthetized patients. *Anesthesiology* 1996;85:A462

33. Schwilden H, Stoeckel H. Quantitative EEG analysis during anaesthesia with isoflurane in nitrous oxide at 1.3 and 1.5 MAC. *British Journal of Anaesthesia* 1987;59:738-745.

34. Schwilden H, Schuttler J, Stoeckel H. Closed-loop feedback control of methohexital anesthesia by quantitative EEG analysis in humans. *Anesthesiology* 1987;67:341-347.

35. Schwilden H, Schuttler J, Stoeckel H. Quantitation of the EEG and pharmacodynamic modelling of hypnotic drugs: etomidate as an example. *European Journal of Anaesthesiology* 1985;2:121-131.

36. Levy WJ. Intraoperative EEG patterns: implications for EEG monitoring. *Anesthesiology* 1984;60:430-434.

37. Liu WH, Thorp TA, Graham SG, Aitkenhead AR. Incidence of awareness with recall during general anaesthesia. *Anaesthesia* 1991;46:435-437.

38. Arndt VM, Hofmockel R, Benad G. EEG-Veranderungen unter Propofol-Alfentanil-Lachgas-Narkose [EEG changes during propofol-alfentanil-nitrous oxide anesthesia]. [German]. *Anaesthesiologie und Reanimation* 1995;20:126-133.

39. Clark DL, Rosner BS. Neurophysiologic effects of general anesthetics. I. The electroencephalogram and sensory evoked responses in man. *Anesthesiology* 1973;38:564-582.

40. Rosner BS, Clark DL. Neurophysiologic Effects of General Anesthetics: II Sequential Regional Actions in the Brain. *Anesthesiology* 1973;39:59-81.

SUBSTITUTE SHEET (RULE 26)

41. Vernon J, Bowles S, Sebel PS, Chamoun N. EEG bispectrum predicts movement at incision during isoflurane or propofol anesthesia. *Anesthesiology* 1992;77:A502

42. Glass P, Sebel P, Greenwald S, Chamoun N. Quantification of the relative effects of anesthetics agents on the EEG and patient responsiveness to incision. *Anesthesiology* 1994;81:A407

43. Lang E, Sebel P, Manberg P. Bispectral EEG Analysis, Analgesia and Movement at Incision During Propofol/Alfentanil/N2O Anesthesia. *Anesthesiology* 1994;81:A476

44. Sebel PS, Rampil I, Cork R, White PF, Smith NT, Glass P, Jopling M, Chamoun N. Bispectral analysis (BIS) for monitoring anesthesia: comparison of anesthetic techniques. *Anesthesiology* 1994;81:A1488

45. Thornton C, Heneghan CP, James MF, Jones JG. Effects of halothane or enflurane with controlled ventilation on auditory evoked potentials. *British Journal of Anaesthesia* 1984;56:315-323.

46. Thornton C, Heneghan CP, Navaratnarajah M, Bateman PE, Jones JG. Effect of etomidate on the auditory evoked response in man. *British Journal of Anaesthesia* 1985;57:554-561.

47. Heneghan CP, Thornton C, Navaratnarajah M, Jones JG. Effect of isoflurane on the auditory evoked response in man. *British Journal of Anaesthesia* 1987;59:277-282.

48. de Beer NA, van Hooff JC, Cluitmans PJ, Korsten HH, Grouls RJ. Haemodynamic responses to incision and sternotomy in relation to the auditory evoked potential and spontaneous EEG. *British Journal of Anaesthesia* 1996;76:685-693.

49. Thornton C, Konieczko K, Jones JG, Jordan C, Dore CJ, Heneghan CP. Effect of surgical stimulation on the auditory evoked response. *British Journal of Anaesthesia* 1988;60:372-378.

SUBSTITUTE SHEET (RULE 26)

50. Schwender D, Golling W, Klasing S, Faber Zullig E, Poppel E, Peter K. Effects of surgical stimulation on midlatency auditory evoked potentials during general anaesthesia with propofol/fentanyl, isoflurane/fentanyl and flunitrazepam/fentanyl. *Anaesthesia* 1994;49:572-578.

51. Sebel PS, Rampil I, Cork R, White P, Smith NT, Brull S, Chamoun N. Bispectral analysis for monitoring anesthesia - a multicenter study. *Anesthesiology* 1993;79:A178

TABLE 1 Mean (range) values of the auditory evoked potentials (AEP) Index, bispectral index (BIS), 95% spectral edge frequency (SEF) and median frequency (MF) during consciousness (consc) and unconsciousness (unconsc).

|  | Unconsc | Consc |
|---|---|---|
| AEP Index | 37.6 (21 - 55) | 60.8 (38 - 98) |
| BIS | 66.8 (40 - 94) | 85.1 (56 - 98) |
| SEF | 18.7 (12.5 - 26.5) | 24.2 (16.1 - 29.1) |
| MF | 8.8 (1.7 - 13.7) | 10.9 (1.5 - 18.9) |

TABLE 2 Values of the auditory evoked potentials (AEP) Index, bispectral index (BIS), 95% spectral edge frequency (SEF) and median frequency (MF) with 100% specificity and values with approximately 85% sensitivity for consciousness and unconsciousness.

|  | Threshold | Sensitivity (%) | Specificity (%) |
|---|---|---|---|
| UNCONSCIOUS | | | |
| AEP Index | 37 | 52 | 100 |
|  | 44 | 85 | 87 |
| BIS | 55 | 15 | 100 |
|  | 76 | 86 | 83 |
| SEF | 16.0 | 9 | 100 |
|  | 21.0 | 85 | 92 |
| MF | 1.4 | 0 | 100 |
|  | 10.7 | 85 | 55 |
| CONSCIOUS | | | |
| AEP Index | 56 | 60 | 100 |
|  | 45 | 87 | 85 |
| BIS | 95 | 14 | 100 |
|  | 75 | 88 | 80 |
| SEF | 26.6 | 15 | 100 |
|  | 21.9 | 84 | 92 |
| MF | 13.8 | 18 | 100 |
|  | 7.9 | 85 | 25 |

APPENDIX 3

*AUDITORY EVOKED POTENTIAL INDEX: A QUANTITATIVE MEASURE OF CHANGES IN AUDITORY EVOKED POTENTIALS DURING GENERAL ANAESTHESIA*

H. MANTZARIDIS and G.N.C. KENNY

H. Mantzaridis, MB ChB, PhD, Senior House Officer, Department of Anaesthetics, Law Hospital NHS Trust, Carluke, Lanarkshire, ML8 5ER, UK and G.N.C. Kenny, BSc(Hons), MD, FRCA, Professor of Anaesthesia, Glasgow University, Department of Anaesthesia, Glasgow Royal Infirmary, 8-16 Alexandra Parade, Glasgow, G31 2ER, UK.

Correspondence to Dr Mantzaridis, please.

Summary

We described a novel index derived from the auditory evoked potential, the auditory evoked potential index, and we compared it with latencies and amplitudes related to clinical signs of consciousness and unconsciousness. Eleven patients, scheduled for total knee replacement under spinal anaesthesia, completed the study. The initial mean (SD) value of the auditory evoked potential index was 72.5 (11.2). During the first period of unconsciousness it decreased to 39.6 (6.9) and returned to 66.8 (12.5) when patients regained consciousness. Thereafter, similar values were obtained whenever patients lost and regained consciousness. Latencies and amplitudes changed in a similar fashion. From all parameters studied, Na latencies had the greatest overlap between successive awake and asleep states. The auditory evoked potential index and Nb latencies had no overlap. The consistent changes demonstrated, suggest that the auditory evoked potential index could be used as a reliable indicator of potential awareness during propofol anaesthesia instead of latencies and amplitudes.

KEY WORDS: Anaesthesia; Anaesthesia, depth of; Anaesthesia, general; Anaesthesia, intravenous; Anaesthesia, monitoring; Awareness; Evoked potentials; Evoked potentials, auditory; Digital signal processing; Propofol.

Introduction

It has been shown that changes in auditory evoked potential (AEP) amplitudes and latencies correlate well with depth of anaesthesia. These changes are similar for equipotent doses of enflurane [1], halothane [2], isoflurane [3], etomidate [4], Althesin [5] and propofol [6] and are partially reversed by surgical stimulation [7].

The main problem associated with the use of AEPs to measure depth of anaesthesia is the complexity of the required methodology. Typically, the raw EEG is divided into 1024-2048 epochs of 80-150 ms, averaged and displayed on the computer screen. Amplitudes and latencies are measured manually off-line. This is acceptable in audiological studies where the data acquisition and processing time can be extended almost indefinitely. In anaesthesia, though, it is inadequate, as the condition of the patient changes much more rapidly and a faster update is required. Lower repetition numbers have been used successfully to provide good quality signals [8-12]. However, reliable peak recognition still remains a problem. Even if this could be performed automatically on-line, we would still be left with the problem of determining which variable reflects depth of anaesthesia best. What is needed is a single numerical parameter extracted from the auditory evoked potentials, which provides an estimate of anaesthetic depth in a simple and reliable manner. Ideally, this parameter should be easy to extract, reliable, not computationally intensive and updated in short, clinically useful intervals. Some aspects of the problem were discussed in an editorial by Sebel and colleagues [13]. They suggested that the final index derived from evoked potentials would probably be a function of both latencies and amplitudes.

A numerical index, based on the average "double differential" of the AEP waveform, was proposed by the Northwick Park group [10,14]. However, no data are available to determine its value.

Using a purpose-built system, we were able to record and process the raw EEG, acquire the AEP and extract an auditory evoked potential index (AEPidx) in real time. This index reflects latencies and amplitudes of the AEP, as suggested by Sebel and colleagues. In this report, we attempted to compare the AEPidx with latencies and amplitudes and relate them to clinical signs of consciousness and unconsciousness.

Patients and Methods

We used data obtained during a previous study, which reported the results of changes in AEP latencies [11]. This study was approved by the Hospital Ethics Committee. Twelve patients who gave their written informed consent underwent total knee replacement under spinal anaesthesia.

The AEP was obtained by averaging 256 epochs of 144 ms duration using a purpose-built PC-based system. The AEP was filtered by a digital 35-point low-pass finite impulse response (FIR) filter with a cut-off frequency of 87 Hz. It was then analysed using a proprietary algorithm which provided us with a single numerical value, reflecting both amplitudes and frequencies of the AEP, the auditory evoked potential index. The AEP curves and the trend of the AEPidx were displayed on the screen, as well as saved on the hard disk for further study.

The AEPidx is a mathematical derivative reflecting the morphology of the AEP. It is calculated as the sum of the square root of the absolute difference between every two successive segments of the AEP waveform [12,15].

Figure 1 shows a three-dimensional graph describing the relationship between amplitude and frequency of a sinusoidal signal and the corresponding AEPidx.

During the procedure, propofol was infused until each patient just lost consciousness and then the patient was allowed to recover. This was repeated several times. Figure 2 shows the display of the computer screen during the procedure. The AEP (and the corresponding AEPidx) was recorded continuously. As a result, we were able to obtain several awake and asleep AEP curves, from which we measured values of latency and amplitude off-line. These values were compared with their respective AEPidx. Statistical analysis was performed on an IBM-compatible computer with *MINITAB For Windows* (version 6.2). We used the Mann-Whitney test (two-sample Wilcoxon rank sum test).

Results

Eleven patients completed the study. The median number of periods of unconsciousness during each procedure was 3 (range 1-6).

We compared the previously reported latencies of peaks Na, Pa and Nb with the peak-to-peak amplitudes Na-Pa and Pa-Nb and the AEPidx at a point 2 minutes after each transition from consciousness to unconsciousness or from unconsciousness to consciousness. These measurements are shown in Table 1 and Figure 3.

From Figure 3 it is fairly obvious that the AEPidx followed all changes in both amplitudes and latencies of the AEP consistently. Before the administration of any anaesthetic, the mean value of the AEPidx was 72.5. It decreased to 39.6 with the first transition from consciousness to unconsciousness and returned to a value slightly lower than the starting one when the patients became conscious again. Thereafter, the same pattern was repeated whenever the patient lost and regained consciousness.

All transitions from consciousness to unconsciousness produced statistically significant changes with the exception of some Na latencies (Table 1). We also compared all variables in pairs during consciousness (Table 2) and unconsciousness (Table 3).

Discussion

At present, AEPs are analysed mostly in terms of amplitudes and latencies of the various peaks. Spectral analysis with the fast Fourier transformation (FFT) has also been used [16-

21]. However, a single number, reflecting the morphology of the AEP, is highly desirable but not yet available.

From a mathematical point of view, the problem can be defined as mapping a two-dimensional vector into a one-dimensional space. Since this is not possible, a data reduction technique, which extracts only the relevant features of the AEP, is required.

We observed that when patients lost consciousness, the amplitudes of the AEP peaks were reduced and their latencies were increased. Those changes occurred almost simultaneously and in the same direction in all patients. Consequently, a measurement that would reflect those changes could be of value.

The number of patients that had some overlap between the conscious and the anaesthetised values depends on the variable measured (Table 4). The AEPidx and the Nb latency were the best in this respect (no overlap) and the Na latency the worst (9 overlaps). This means that there was no patient who had an awake AEPidx lower than (or an awake Nb latency greater than) an unconscious value. Obviously, the more the overlap the less the certainty that the variable in question can differentiate between the conscious and the anaesthetised state.

This is in agreement with the findings of Thornton and colleagues [22] who found that the Nb latency was the best feature distinguishing the "three wave" AEP pattern (indicative of light anaesthesia) from the "two wave" pattern, which corresponded to deeper levels. Nb latencies less than 44.5 ms were associated with a high incidence of responses and with very light anaesthesia. They concluded that the MLAEPs reflect the change between wakefulness and unconsciousness. However, they stated that further studies were needed to develop pattern recognition techniques of the AEP and to allow on-line analysis if it were to provide a clinical indicator of awareness.

The AEPidx has three main advantages over the conventional methods of describing the AEP in terms of latencies and amplitudes:

SUBSTITUTE SHEET (RULE 26)

- It is easy to calculate.
- The calculation can be performed in real time.
- It provides a single numerical variable that describes the underlying morphology of the AEP.

It is interesting to note that the mean awake AEPidx became progressively lower (Table 1). Although this did not reach statistical significance, it may indicate the residual sedative effect of propofol.

The AEPidx is not perfect. It is affected by muscle and movement artefacts, diathermy and other electrical theatre interference. However, these sources of potential error are eliminated by the rigorous artefact rejection algorithms and the low-pass filtering to which the signals are subjected [11].

Conclusions

The auditory evoked potential index is a single numerical parameter extracted from the AEP using a proprietary data compression algorithm. In the present study, it was shown to change according to the patients' state in a consistent and reproducible fashion. It has a clear advantage over the Nb latency in the determination of awareness, since it can be extracted from the AEP in a rapid and reproducible fashion. More studies are required to evaluate its usefulness and, ultimately, determine whether it represents a true measure of depth of anaesthesia.

References

1. Thornton C, Catley DM, Jordan C, Lehane JR, Royston D, Jones JG. Enflurane anaesthesia causes graded changes in the brainstem and early cortical auditory evoked response in man. *British Journal of Anaesthesia* 1983; 55: 479-486.

2. Thornton C, Heneghan CP, James MF, Jones JG. Effects of halothane or enflurane with controlled ventilation on auditory evoked potentials. *British Journal of Anaesthesia* 1984; 56: 315-323.

3. Heneghan CP, Thornton C, Navaratnarajah M, Jones JG. Effect of isoflurane on the auditory evoked response in man. *British Journal of Anaesthesia* 1987. 59: 277-282.

4. Thornton C, Heneghan CP, Navaratnarajah M, Bateman PE, Jones JG. Effect of etomidate on the auditory evoked response in man. *British Journal of Anaesthesia* 1985; 57: 554-561.

5. Thornton C, Heneghan CP, Navaratnarajah M, Jones JG. Selective effect of althesin on the auditory evoked response in man. *British Journal of Anaesthesia* 1986; 58, 422-427.

6. Thornton C, Konieczko KM, Knight AB, Kaul B, Jones JG, Dore CJ, White DC. Effect of propofol on the auditory evoked response and oesophageal contractility *British Journal of Anaesthesia* 1989: 63: 411-417.

7. Thornton C, Konieczko K, Jones JG, Jordan C, Dore CJ, Heneghan CP Effect of surgical stimulation on the auditory evoked response. *British Journal of Anaesthesia* 1988; 60. 372-378.

8. Goldstein R, Rodman LB, Karlovich RS. Effects of stimulus rate and number on the early components of the averaged electroencephalographic response. *Journal of Speech and Hearing Research* 1972; 15: 559-566.

9. McFarland WH, Vivion MC, Wolf KE, Goldstein R. Reexamination of effects of stimulus rate and number on the middle components of the averaged electroencephalographic response. *Audiology* 1975; 14: 456-465.

10. Thornton C, Newton DEF. The auditory evoked response: a measure of depth of anaesthesia. *Bailliere's Clinical Anaesthesiology* 1989; 3: 559-585.

11. Davies FW, Mantzaridis H, Kenny GN, Fisher AC. Middle latency auditory evoked potentials during repeated transitions from consciousness to unconsciousness. *Anaesthesia* 1996; 51: 107-113.

12. Mantzaridis H. *Closed-loop control of anaesthesia*. PhD Thesis, University of Strathclyde, 1996.

13. Sebel PS, Heneghan CP, Ingram DA. Evoked responses-a neurophysiological indicator of depth of anaesthesia? (editorial). *British Journal of Anaesthesia* 1985; 57: 841-842.

14. Thornton C. Evoked potentials in anaesthesia. *European Journal of Anaesthesiology* 1991; 8: 89-107.

15. Doi M, Gajraj RJ, Mantzaridis H, Kenny GN. Relationship between calculated blood concentration of propofol and electrophysiological variables during emergence from anaesthesia: a comparison of Bispectral Index, spectral edge frequency, median frequency and Auditory Evoked Potential Index. *British Journal of Anaesthesia* (In Press).

16. Madler C, Poppel E. Auditory evoked potentials indicate the loss of neuronal oscillations during general anaesthesia. *Naturwissenschaften* 1987; 74: 42-43.

17. Madler C, Keller I, Schwender D, Poppel E. Sensory information processing during general anaesthesia: effect of isoflurane on auditory evoked neuronal oscillations. *British Journal of Anaesthesia* 1991; 66: 81-87.

18. Schwender D, Klasing S, Madler C, Poppel E, Peter K. Mid-latency auditory evoked potentials during ketamine anaesthesia in humans. *British Journal of Anaesthesia* 1993; 71: 629-632.

19. Schwender D, Rimkus T, Haessler R, Klasing S, Poppel E, Peter K. Effects of increasing doses of alfentanil, fentanyl and morphine on mid-latency auditory evoked potentials. *British Journal of Anaesthesia* 1993; 71: 622-628.

20. Schwender D, Faber Zullig E, Klasing S, Poppel E, Peter K. Motor signs of wakefulness during general anaesthesia with propofol, isoflurane and flunitrazepam/fentanyl and midlatency auditory evoked potentials. *Anaesthesia* 1994; 49: 476-484.

21. Schwender D, Golling W, Klasing S, Faber Zullig E, Poppel E, Peter K. Effects of surgical stimulation on midlatency auditory evoked potentials during general anaesthesia with propofol/fentanyl, isoflurane/fentanyl and flunitrazepam/fentanyl. *Anaesthesia* 1994; 49: 572-578.

22. Thornton C, Barrowcliffe MP, Konieczko KM, Ventham P, Dore CJ, Newton DE, Jones JG. The auditory evoked response as an indicator of awareness. *British Journal of Anaesthesia* 1989; 63: 113-115.

- 68 -

| | | Start (n=11) | UNCON 1 (n=11) | CON 1 (n=11) | UNCON 2 (n=10) | CON 2 (n=10) | UNCON 3 (n=8) | CON 3 (n=8) |
|---|---|---|---|---|---|---|---|---|
| AEPidx | Mean | 72.5 | 39.6 | 66.8 | 39.7 | 65.3 | 38.9 | 61.8 |
| | SD | 11.2 | 6.9 | 12.5 | 5.4 | 8.9 | 2.4 | 9.5 |
| | | | p=0.0001 | p=0.0002 | p=0.0002 | p=0.0002 | p=0.0004 | p=0.0009 |
| Na-Pa (μV) | Mean | 2.2 | 0.9 | 1.8 | 0.9 | 1.8 | 1.0 | 1.9 |
| | SD | 0.4 | 0.4 | 0.4 | 0.4 | 0.6 | 0.4 | 0.4 |
| | | | p=0.0001 | p=0.0009 | p=0.0008 | p=0.0005 | p=0.0049 | p=0.0027 |
| Pa-Nb (μV) | Mean | 1.8 | 0.7 | 1.5 | 0.8 | 1.7 | 0.7 | 1.6 |
| | SD | 0.7 | 0.4 | 0.4 | 0.2 | 0.8 | 0.3 | 0.8 |
| | | | p=0.0002 | p=0.0008 | p=0.0012 | p=0.0021 | p=0.0043 | p=0.003 |
| Na (ms) | Mean | 20.0 | 22.5 | 21.3 | 23.2 | 21.7 | 23.1 | 21.3 |
| | SD | 1.4 | 2.0 | 1.4 | 1.5 | 1.2 | 1.7 | 1.4 |
| | | | p=0.004 | p=0.136 | p=0.016 | p=0.035 | p=0.095 | p=0.065 |
| Pa (ms) | Mean | 31.7 | 39.3 | 33.5 | 39.2 | 33.6 | 39.7 | 33.3 |
| | SD | 1.0 | 2.1 | 1.2 | 2.7 | 2.4 | 3.6 | 3.3 |
| | | | p=0.0001 | p=0.0001 | p=0.001 | p=0.001 | p=0.004 | p=0.009 |
| Nb (ms) | Mean | 42.8 | 57.8 | 44.6 | 58.9 | 43.9 | 59.1 | 46.3 |
| | SD | 1.6 | 4.4 | 2.1 | 4.6 | 3.0 | 5.9 | 3.1 |
| | | | p=0.0001 | p=0.0001 | p=0.0001 | p=0.0002 | p=0.0004 | p=0.0009 |

Table 1 Auditory evoked potential latencies and amplitudes and the AEPidx during successive transitions from consciousness (CON) to unconsciousness (UNCON). Mean, standard deviation (SD) and statistical significance (p).

| | | Start | CON 1 | CON 2 |
|---|---|---|---|---|
| AEPidx | CON 1 | 0.3084 | | |
| | CON 2 | 0.1586 | 0.8324 | |
| | CON 3 | 0.0517 | 0.3629 | 0.5620 |
| Na-Pa (μV) | CON 1 | 0.0442 | | |
| | CON 2 | 0.0282 | 0.9156 | |
| | CON 3 | 0.1958 | 0.3843 | 0.3215 |
| Pa-Nb (μV) | CON 1 | 0.3387 | | |
| | CON 2 | 0.8868 | 0.4795 | |
| | CON 3 | 0.4279 | 0.8346 | 0.6867 |
| Na (ms) | CON 1 | 0.0316 | | |
| | CON 2 | 0.0029 | 0.5433 | |
| | CON 3 | 0.0580 | 1.000 | 0.6192 |
| Pa (ms) | CON 1 | 0.0032 | | |
| | CON 2 | 0.0248 | 0.9432 | |
| | CON 3 | 0.0793 | 0.6464 | 0.8936 |
| Nb (ms) | CON 1 | 0.0202 | | |
| | CON 2 | 0.1251 | 0.6439 | |
| | CON 3 | 0.0113 | 0.1329 | 0.0814 |

SUBSTITUTE SHEET (RULE 26)

Table 2 Statistical significance (p) of comparisons between conscious states for all studied AEP parameters. Underlined results indicate significant difference at the 95% level.

|  |  | UNCON 1 | UNCON 2 |
|---|---|---|---|
| AEPidx | UNCON 2 | 0.7234 | |
| | UNCON 3 | 0.6467 | 0.8932 |
| Na-Pa (μV) | UNCON 2 | 0.6700 | |
| | UNCON 3 | 0.4785 | 0.8233 |
| Pa-Nb (μV) | UNCON 2 | 0.3756 | |
| | UNCON 3 | 0.9011 | 0.3947 |
| Na (ms) | UNCON 2 | 0.4348 | |
| | UNCON 3 | 0.5888 | 0.8930 |
| Pa (ms) | UNCON 2 | 0.5702 | |
| | UNCON 3 | 0.5607 | 0.5029 |
| Nb (ms) | UNCON 2 | 1.0000 | |
| | UNCON 3 | 0.7404 | 0.8586 |

Table 3 Statistical significance (p) of comparisons between unconscious states for all studied AEP parameters.

| | AEPidx | Na-Pa (μV) | Pa-Nb (μV) | Na (ms) | Pa (ms) | Nb (ms) |
|---|---|---|---|---|---|---|
| Overlap | 0 | 1 | 4 | 9 | 2 | 0 |
| No overlap | 11 | 10 | 7 | 2 | 9 | 11 |

Table 4 Number of patients in which the awake parameters overlapped with the asleep values.

Legends for figures

Figure 1: Three-dimensional plot of the AEPidx against amplitude ($10^{-7}$ V) and frequency (Hz).

Figure 2: A typical AEPidx trace as displayed on the computer screen during surgery. Target blood propofol concentration is also shown (black area at the bottom of the screen). A= unconscious, B= conscious. At point C, the propofol infusion was increased in steps until the patient lost consciousness again. At point D, the propofol target was set again to zero.

Figure 3: Changes in AEP latencies and amplitudes and in the AEPidx during repeated periods of consciousness and unconsciousness (mean and standard deviation).

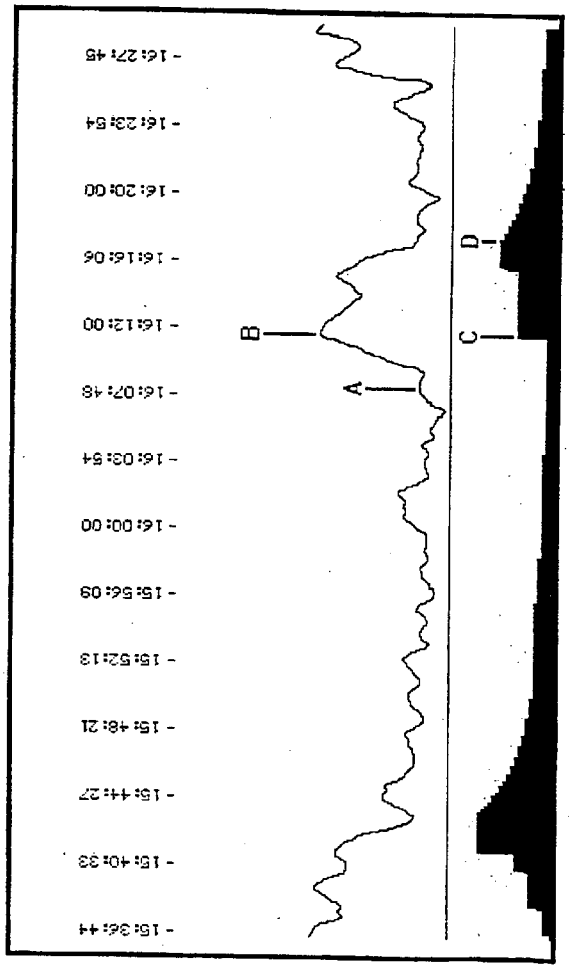

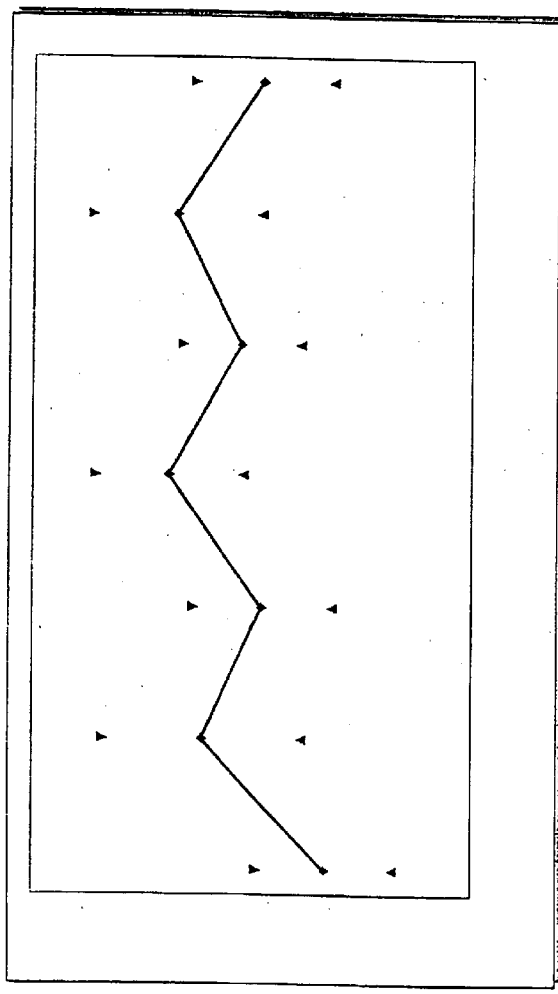

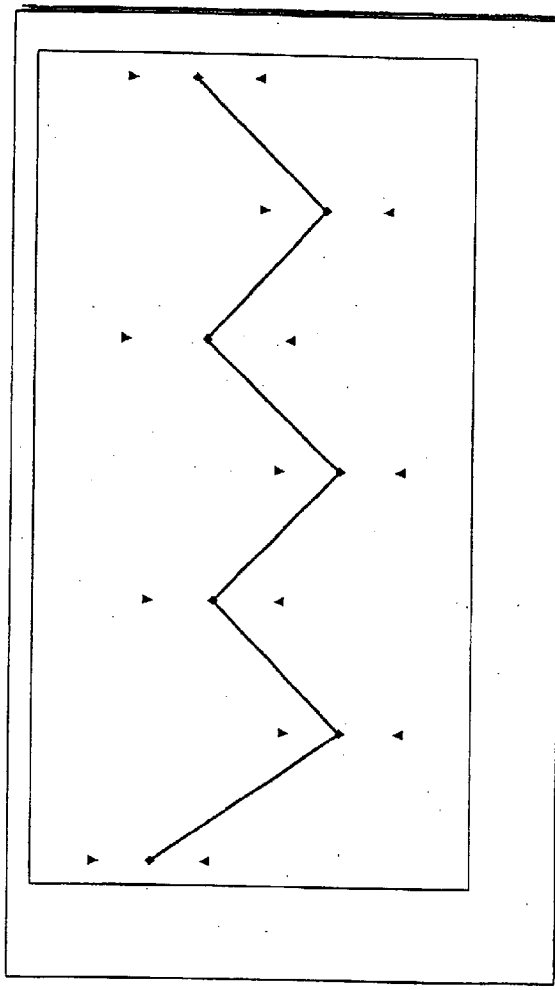

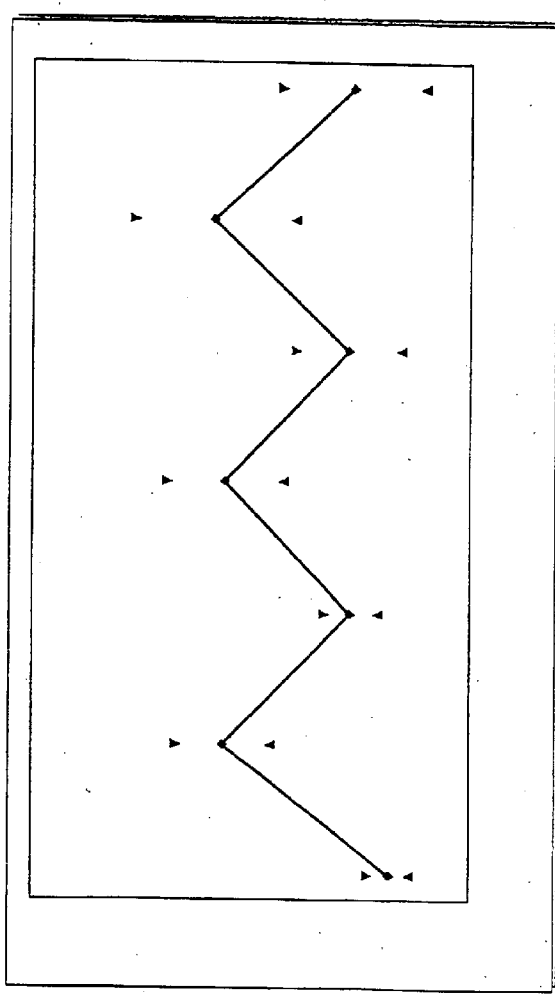

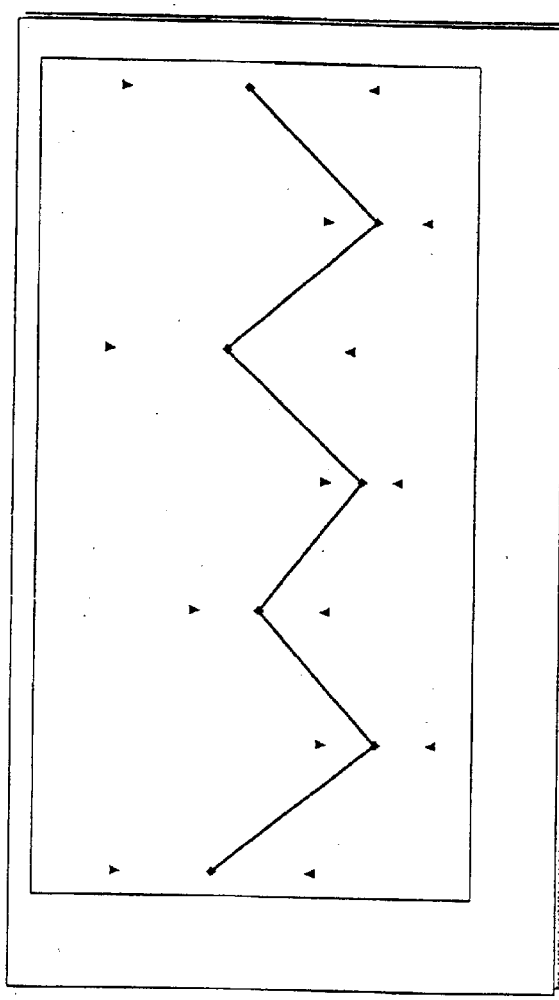

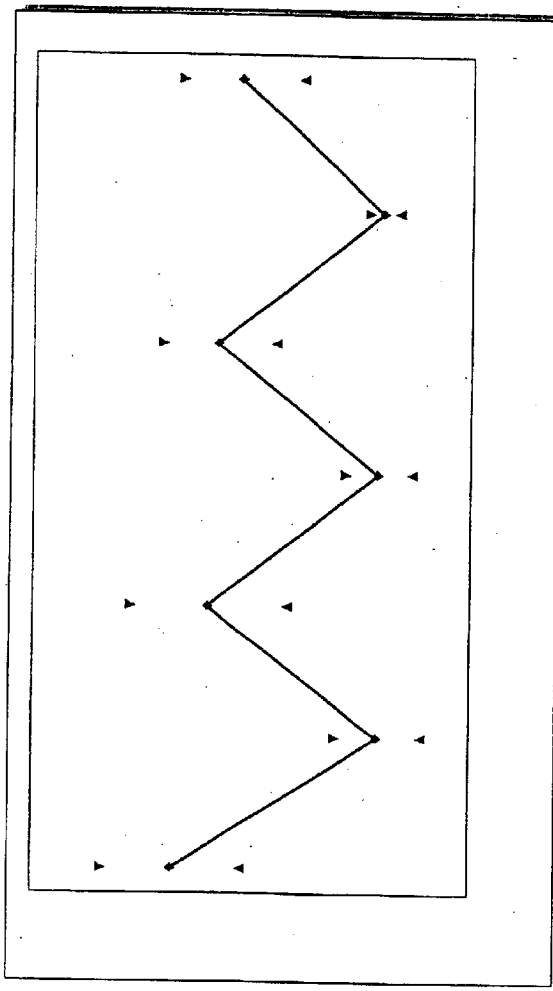
- 76 -

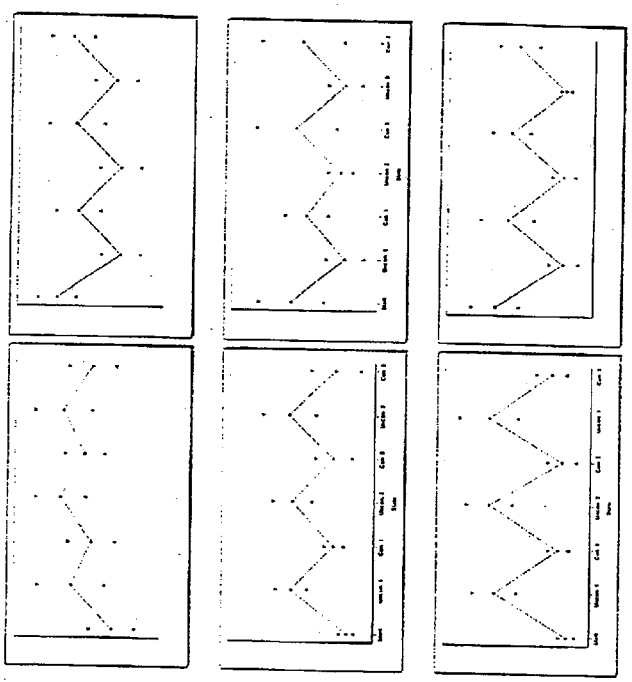

What is claimed is:

1. A method of calculating an index indicative of anaesthetic depth, the method comprising:
    subjecting a patient to a repetitive audio stimulus;
    monitoring auditory evoked potentials (AEP) produced by the patient;
    providing a signal corresponding to the coarseness of the monitored AEP signal, the coarseness of the signal being a single measure increasing and decreasing with both amplitude and frequency of variations in the signal AEP signal; and
    using said signal as said index indicative of anaesthetic depth.

2. A method as claimed in claim 1 wherein the monitored or raw AEP signal is divided into a series of sweeps or frames of a given duration, each sweep being synchronised with the repetitive audio stimulus.

3. A method as claimed in claim 2 wherein a number of sweeps n are recorded in sequence and are averaged to produce a time averaged sweep and for the time averaged sweep the anaesthesia index is calculated.

4. A method as claimed in claim 3 wherein each time a new series of sweeps is recorded, a new time averaged sweep is determined from the most recent n sweeps and the anaesthesia index for that time averaged sweep calculated.

5. A method as claimed in claim 4, wherein for a moving time averaged sweep this measure is a function of the sum of the square roots of the difference between every two adjacent sample points in the time averaged sweep.

6. A method as claimed in claim 2 wherein the raw AEP signal is sampled at regular intervals to produce a digitized AEP signal.

7. A method as claimed in claim 2 wherein an indication of coarseness is obtained by measuring the differences between neighboring sample points.

8. A method as claimed in claim 3 wherein the raw AEP signal is sampled at regular intervals to produce a digitized AEP signal.

9. A method as claimed in claim 3 wherein an indication of coarseness is obtained by measuring the differences between neighboring sample points.

10. A method as claimed in claim 3, wherein said index is calculated and used without reference to a measured amplitude of the time averaged sweep.

11. A method as claimed in claim 3, wherein said index is calculated and used without reference to a measured EEG power.

12. A method as claimed in claim 4 wherein the raw AEP signal is sampled at regular intervals to produce a digitized AEP signal.

13. A method as claimed in claim 4 wherein an indication of coarseness is obtained by measuring the differences between neighboring sample points.

14. A method as claimed in claim 1 wherein the raw AEP signal is sampled at regular intervals to produce a digitized AEP signal.

15. A method as claimed in claim 1 wherein an indication of coarseness is obtained by measuring the differences between neighboring sample points.

16. A method as claimed in claim 1, wherein said index is calculated and used without reference to a measured latency of any peak in the AEP signal.

17. A method as claimed in claim 1, wherein said index is calculated and used without relying on data measured previously for the same patient at a known depth of anaesthesia.

18. A method of maintaining closed-loop control of an anaesthesia depth, the method comprising supplying a dosage of anaesthetic to a patient, calculating an anaesthetic depth index according to claim 1, and using the value of the anaesthetic depth index to regulate the anaesthetic supply to maintain the anaesthesia depth index at or near a predetermined level.

19. A system for calculating an index of anaesthetic depth, the system comprising: a signal generator for subjecting patient to a repetitive audio stimulus, electroencephalographic (EEG) recording means for coupling to said patient for recording auditory evoked potential (AEP) signal from the patient, and computer means for receiving said AEP signal, and for processing said AP signals and generating an index signal indicative of the coarseness of the recorded AEP signal, the coarseness of the signal being a single measure increasing and decreasing with both amplitude and frequency variations of the AEP signal, said index signal being representative of the depth of anaesthesia.

20. An anaesthetic supply control system including a system for calculating an index of anaesthetic depth for a patient as claimed in claim 19, including anaesthetic supply means and a regulator for receiving said input signal, said regulator having received a predetermined anaesthetic depth index and said regulator comparing said index signal and said predetermined signal and providing a control signal to said anaesthetic supply means for regulating the supply of anaesthetic to the patient to maintain the anaesthetic depth index at a predetermined level.

21. A system as claimed in claim 19, wherein said computer means is arranged to measure coarseness by reference to difference between neighboring samples of the AEP signal.

22. A system as claimed in claim 21 wherein said computer means is arranged to measure coarseness by summing the square roots of the differences between neighboring samples of the AEP signal.

23. A system as claimed in claim 19, wherein said index is calculated and used without reference to a measured latency of any peak in the AEP signal.

24. A system as claimed in claim 23, wherein said index is calculated and used without reference to a measured amplitude of the time averaged sweep.

25. A system as claimed in claim 24, wherein said index is calculated and used without separately measuring EEG power.

26. A system as claimed in claim 19, wherein said index is calculated an used without relying on data measured previously for the same patient at a known depth of anaesthesia.

27. A method of calculating an index indicative of anaesthetic depth, comprising:
    subjecting a patient to a repetitive audio stimulus;
    monitoring audio evoked potential (AEP) signals produced by the patient; and
    providing a signal corresponding to the coarseness of the monitored AEP signal, and using said signal as an index indicative of anaesthetic depth, the coarseness of the signal being a measure of curvature in the AEP signal.

28. A method of calculating an index indicative of anaesthetic depth, comprising:
    subjecting a patient to a repetitive audio stimulus;
    monitoring audio evoked potential (AEP) signals produced by the patient; and
    providing a signal corresponding to the coarseness of the monitored AEP signal, and using said signal as an index indicative of anaesthetic depth, the coarseness of the signal being obtained as a mathematical derivative with respect to time of the AEP signal.

29. A system for calculating an index of anaesthetic depth, the system comprising:

a signal generator for subjecting a patient to repetitive audio stimulus;

electroencephalographic (EEG) recording means for coupling to said patient for recording an auditory evoked potential (AEP) signal; and a processor for processing successive AEP signals to generate and index signal by measuring the coarseness of the recorded AEP signal, the coarseness of the signal being obtained as a mathematical derivative with respect to time of the AEP signal, said index being indicative of the depth of anaesthesia of the patient.

30. A system for calculating an index of anaesthetic depth, the system comprising:

a signal generator for subjecting a patient to repetitive audio stimulus;

electroencephalographic (EEG) recording means for coupling to said patient for recording an auditory evoked potential (AEP) signal; and a processor for processing successive AEP signals to generate and index signal by measuring the coarseness of the recorded AEP signal; the coarseness of the signal being obtained by differentiating the AEP signal with respect to time, said index being indicative of the depth of anaesthesia of the patient.

* * * * *